United States Patent
Pan et al.

(10) Patent No.: US 12,310,960 B2
(45) Date of Patent: May 27, 2025

(54) COMBINATIONAL USES OF NITROXOLINE AND ITS ANALOGUES WITH CHEMOTHERAPIES AND IMMUNOTHERAPIES IN THE TREATMENT OF CANCERS

(71) Applicant: Jiangsu Yahong Meditech Co., Ltd., Taizhou Jiangsu (CN)

(72) Inventors: Ke Pan, Chadds Ford, PA (US); Peng Huang, Okayama (JP); Qiang Li, China Medical (CN)

(73) Assignee: Jiangsu Yahong Meditech Co., Ltd., Taizhou Jiangsu (CN)

( * ) Notice: Subject to any disclaimer, the term of this patent is extended or adjusted under 35 U.S.C. 154(b) by 510 days.

(21) Appl. No.: 17/656,903

(22) Filed: Mar. 29, 2022

(65) Prior Publication Data

US 2022/0218692 A1  Jul. 14, 2022

Related U.S. Application Data

(62) Division of application No. 16/089,800, filed as application No. PCT/US2017/025388 on Mar. 31, 2017, now Pat. No. 11,324,739.

(60) Provisional application No. 62/315,774, filed on Mar. 31, 2016.

(51) Int. Cl.
| | |
|---|---|
| *A61K 31/47* | (2006.01) |
| *A61K 9/00* | (2006.01) |
| *A61K 31/282* | (2006.01) |
| *A61K 31/337* | (2006.01) |
| *A61K 31/407* | (2006.01) |
| *A61K 31/704* | (2006.01) |
| *A61K 33/243* | (2019.01) |
| *A61K 39/00* | (2006.01) |
| *A61K 39/04* | (2006.01) |
| *A61K 39/395* | (2006.01) |
| *A61P 35/00* | (2006.01) |
| *C07K 16/28* | (2006.01) |

(52) U.S. Cl.
CPC ............ *A61K 31/47* (2013.01); *A61K 9/0019* (2013.01); *A61K 9/0053* (2013.01); *A61K 31/282* (2013.01); *A61K 31/337* (2013.01); *A61K 31/407* (2013.01); *A61K 31/704* (2013.01); *A61K 33/243* (2019.01); *A61K 39/04* (2013.01); *A61K 39/3955* (2013.01); *A61P 35/00* (2018.01); *C07K 16/2818* (2013.01); *A61K 2039/505* (2013.01); *A61K 2039/54* (2013.01); *C07K 2317/76* (2013.01)

(58) Field of Classification Search
CPC ............ A61P 13/10; A61P 35/00; A61K 31/47
See application file for complete search history.

(56) References Cited

U.S. PATENT DOCUMENTS

| | | |
|---|---|---|
| 6,090,385 A | 7/2000 | Maes |
| 8,729,097 B2 | 5/2014 | Liu |
| 9,758,484 B2 | 9/2017 | Pan |
| 10,212,090 B2 | 2/2019 | Zhang |
| 2009/0217401 A1 | 8/2009 | Korman |
| 2010/0247440 A1 | 9/2010 | Morton |
| 2011/0098456 A1 | 4/2011 | Uhlmann |
| 2011/0212090 A1 | 9/2011 | Pedersen |
| 2013/0309250 A1 | 11/2013 | Cogswell |
| 2014/0336248 A1* | 11/2014 | Ma ................... A61P 35/00 435/375 |
| 2014/0371285 A1 | 12/2014 | Sprott |
| 2015/0190413 A1 | 7/2015 | Chaber |
| 2015/0284455 A1 | 10/2015 | Springer |
| 2016/0031819 A1 | 2/2016 | Pan |
| 2016/0361298 A1 | 12/2016 | Novick |
| 2017/0007686 A1 | 1/2017 | Glick |
| 2018/0104455 A1 | 4/2018 | Geva |
| 2018/0273948 A1 | 9/2018 | Kadiyala |
| 2019/0262444 A1 | 8/2019 | Mahr |

FOREIGN PATENT DOCUMENTS

| | | |
|---|---|---|
| CN | 105228984 A | 1/2016 |
| JP | 2011505370 A | 2/2011 |
| JP | 2015518826 A | 7/2015 |
| WO | 2006091871 A1 | 8/2006 |
| WO | 2009091904 A2 | 7/2009 |

OTHER PUBLICATIONS

Alibek, Kenneth, et al., "Using antimicrobial adjuvant therapy in cancer treatmeent: a review," Infectious Agents and Cancer, vol. 7:33, (2012).
Neve et al., Cancer Cell, 2006; 10: 515-527 (Year: 2006).
Matsushima M., et al., "Enhanced antitumor effect of combination intravesical mitomycin C and bacillus Calmette-Guerin therapy in an orthotopic bladder cancer model," Oncology Letters, vol. 2, pp. 13-19 (2011).
Li, Q. et al., "Abstract 2037: Oral nitroxoline in combination with intravesical bacille calmette-guerin (BCG) shows synergistic anti-tumor efficacy in mouse bladder cancer orthotopic xenograft," Cancer Research, vol. 77, Supp. 13, pp. 1-4 (2017).
Gu X., et al., "Neoadjuvant chemotherapy of breast cancer with pirarubicin versus epirubicin in combination with cyclophosphamide and docetaxel," Tumor Biology, vol. 36, pp. 5529-5535 (2015).
Yasuda, et al., "Simultaneous blockade of programmed death 1 and vascular endothelial growth factor receptor 2 (VEGFR2) induces synergistic anti-tumour effect in vivo", Clinical and Experimental Immunology, vol. 172, No. 3, pp. 500-506, (Apr. 2013).

(Continued)

*Primary Examiner* — Brian Gangle
*Assistant Examiner* — Lakia J Jackson-Tongue
(74) *Attorney, Agent, or Firm* — Ice Miller LLP

(57) ABSTRACT

Novel combination therapies involving nitroxoline, its analogue or pharmaceutically acceptable salt thereof with at least one additional anti-cancer chemotherapy or immunotherapy agent are described. Related kits, pharmaceutical compositions and methods of production arlinee also described.

9 Claims, 9 Drawing Sheets

(56) References Cited

OTHER PUBLICATIONS

Xu, et al., "The Novel Combination of Nitroxoline and PD-1 Blockade, Exerts a Potent Antitumor Effect in a Mouse Model of Prostate Cancer", International Journal of Biological Sciences, vol. 15, No. 5, pp. 919-928, (Jan. 2019).
Veschi, et al., Effects of repurposed drug candidates nitroxoline and nelfinavir as single agents or in combination with erlotinib in pancreatic cancer cells, J. Exp. Clin. Cancer. Res., vol. 37, No. 236, (13 pages), (2018).
Yang, et al., "Combined effects of Cantide and chemoterapeutic drugs on inhibition of tumor cells' growth in vitro and in vivo", World J Gastroenterol, vol. 11, No. 16, pp. 2491-2496, (2005).
Adlard et al., "Rapid Restoration of Cognition in Alzheimer's Transgenic Mice with 8-Hydroxy Quinoline Analogs is Associated with Decreased Interstitial Ab," Neuron, vol. 59, pp. 43-55 (Jul. 10, 2008).
Chang et al., "Repurposing of nitroxoline as a potential anticancer agent against human prostate cancer—a crucial role on AMPK/mTOR signaling pathway and the interplay with Chk2 activation," Oncotarget, vol. 6, No. 37, pp. 39806-39820 (2015).
Chou et al., "Experimental Design, and Computerized Simulation of Synergism and Antagonism in Drug Combination Studies," Pharmacol. Rev., vol. 58, pp. 621-681 (2006).
Ding et al., "Anticancer Activity of the Antibiotic Clioquinol," Cancer Res., vol. 65, pp. 3389-3395 (2005).
Fraser et al., "The Mechanism of Inhibition of Ribonucleic Acid Synthesis by 8-Hydroxyquinoline and the Antibiotic Lomofungin," Biochem J., vol. 147, pp. 401-410 (1975).
Freeman et al., "Engagement of the PD-1 immunoinhibitory receptor by a novel B7 family member leads to negative regulation of lymphocyte activation," J. Exp. Med., vol. 192, pp. 1027-1034 (2000).
Fuge et al., "Immunotherapy for bladder cancer," Research and Reports in Urology, vol. 7, pp. 65-79 (2015).
Hamid et al., "Safety and tumor responses with lambrolizumab (anti-PD-1) in melanoma," N. Engl. J. Med, vol. 369, No. 2, pp. 134-144 (2013).
Hawkes et al., "Programmed cell death-1 inhibition in lymphoma," Lancet. Oncol., vol. 16, No. 5, pp. e234-e245 (2015).
Huang et al., "Efficacy of intravesical Bacillus Calmette-Guerin therapy against tumor immune escape in an orthotopic model of bladder cancer," Exp. Ther. Med., vol. 9, No. 1, pp. 162-166 (2015).
International Search Report issued Jun. 20, 2017 in International Application No. PCT/US2017/025388.
Jiang et al., "Nitroxoline (5-amino-8-hydroxyquinoline) is more a potent anti-cancer agent than clioquinol (5-chloro-7-8-quinoline)," Cancer Letters, vol. 312, pp. 11-17 (2011).
Krummel et al., "CD28 and CTLA-4 have opposing effects on the response of T cells to stimulation," J. Exp. Md., vol. 182, No., 2, pp. 459-465 (1995).
Liu et al., "Selective inhibition of ID01 effectively regulates mediators of antitumor immunity," Blood, vol. 115, pp. 3520-3530 (2010).
Muller et al., Marrying Immunotherapy with Chemotherapy: Why Say IDO?, Cancer Res., vol. 65, pp. 8065-8068 (2005).
Opitz et al., "The Indoleamine-2,3-Dioxygenase (IDO) Inhibitor 1-Methyl-D-tryptophan Upregulates ID01 in Human Cancer Cells," PloS One, vol. 6, No. 5, e19823, pp. 1-11 (2011).
Pardoll, "The blockade of immune checkpoints in cancer immunotherapy," Nat. Rev. Cancer, vol. 12, No. 4, pp. 252-264 (2012).
Pelletier et al., "Roles of Divalent Cations and pH in mechanism of Action of Nitroxoline against *Escherichia coli* Strains," Antimicrobial Agents and Chemotherapy, vol. 39, No. 3, pp. 707-713 (Mar. 1995).
Joong Sup Shim et al, "Effect of Nitroxoline on Angiogenesis and Growth of Human Bladder Cancer", Journal of the National Cancer Institute, United States, doi:10.1093/jnci/djq457, (Dec. 15, 2010), pp. 1855-1873, URL: https://academic.oup.com/jnci/article-pdf/102/24/1855/17310783/djq457.pdf, XP055633839.
Whiteside, T. L, "Inhibiting the Inhibitors: Evaluating Agents Targeting Cancer Immunosuppression," Expert Opinion Biol. Ther., vol. 10, No. 7, pp. 1019-1035 (2010).
Yan et al., "A formal model for analyzing drug combination effects and its application in TNF-a-induced NFkB pathway," BMC Syst. Biol., vol. 4, No. 50, pp. 1-12 (2010).
Philips et all., International Immunology, 2014; 27(1);39-46 (Year: 2014).
Unofficial translation of CN 105228984 (Year: 2016).

* cited by examiner

Oxyquinoline    Clioquinol    Iodoquinol    Nitroxoline

Figure 9
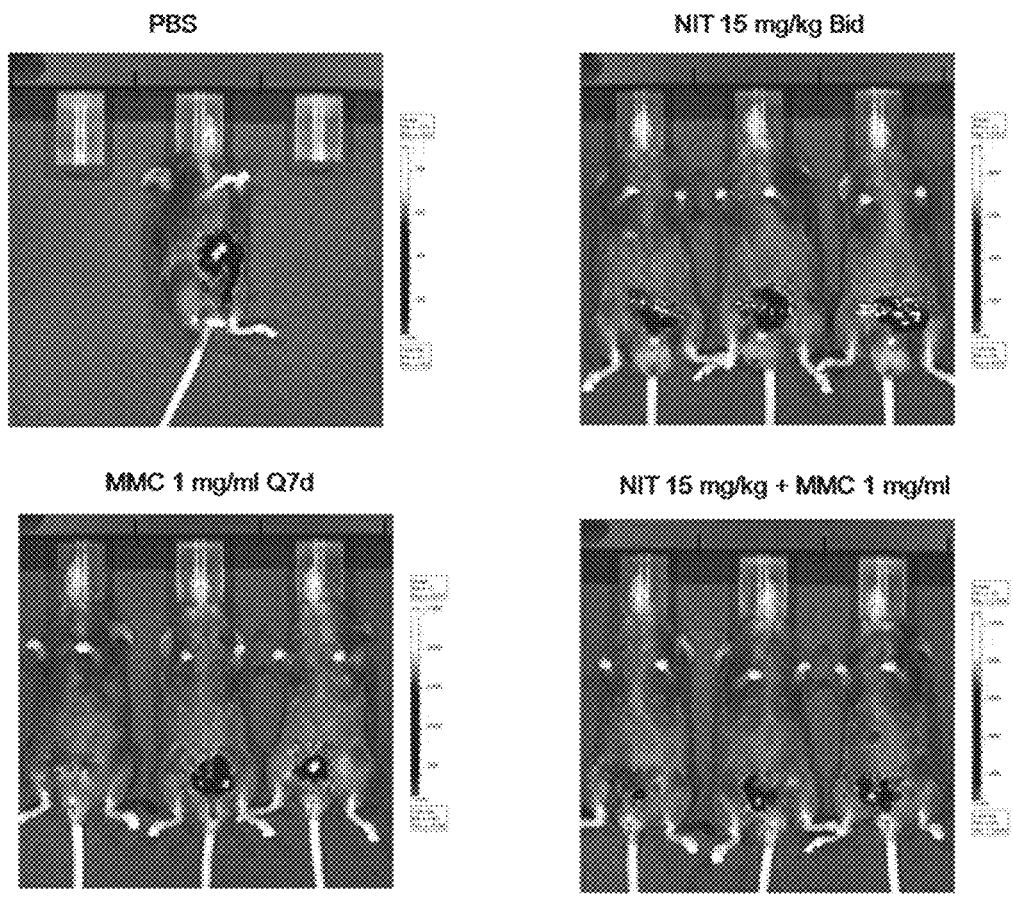
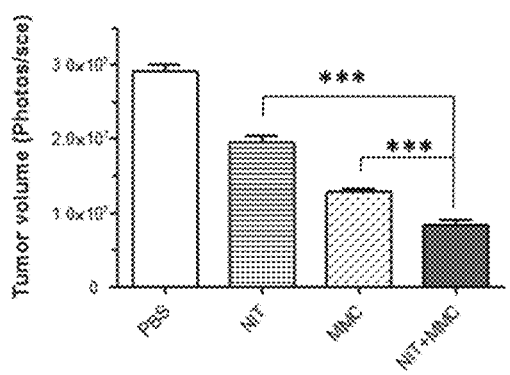
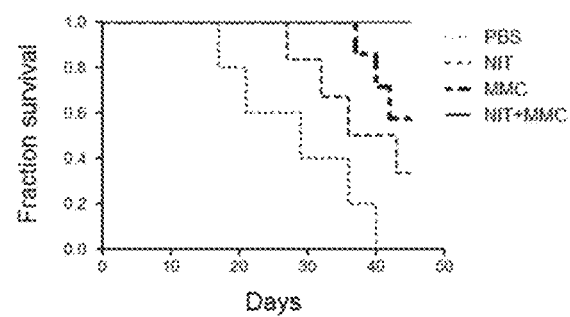

Figure 11
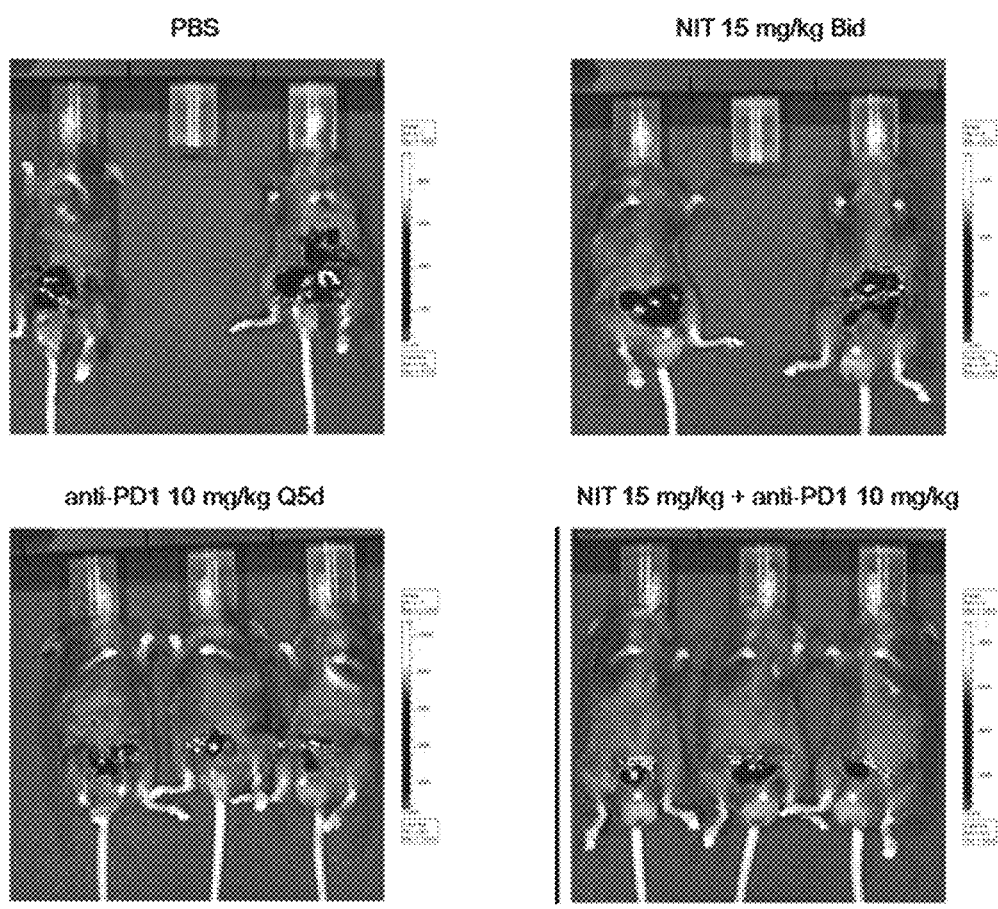
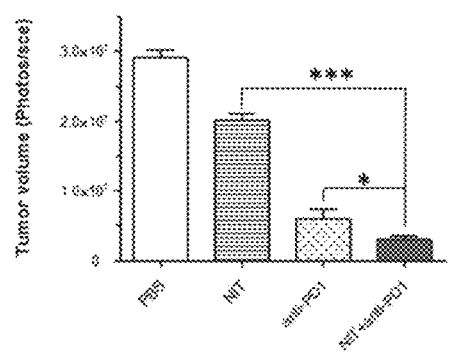
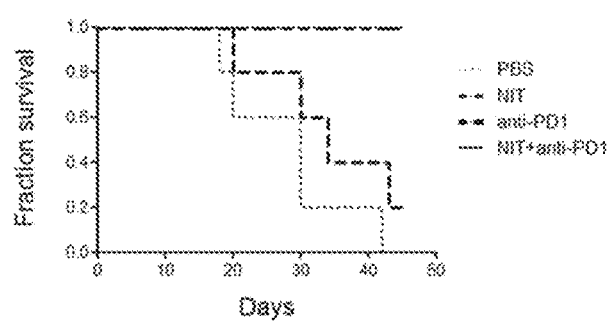

COMBINATIONAL USES OF NITROXOLINE AND ITS ANALOGUES WITH CHEMOTHERAPIES AND IMMUNOTHERAPIES IN THE TREATMENT OF CANCERS

CROSS REFERENCE TO RELATED APPLICATIONS

This application is a divisional application of U.S. patent application Ser. No. 16/089,800 filed Sep. 28, 2018, allowed, which is a Section 371 of International Application No. PCT/US2017/025388, filed Mar. 31, 2017, which published in the English Language on Oct. 5, 2017, under International Publication No. WO 2017/173278, which claims priority to U.S. Provisional Patent Application No. 62/315,774, filed on Mar. 31, 2016, the disclosures of which are hereby incorporated by reference herein in their entirety.

FIELD OF THE INVENTION

The present invention relates to a combination therapy for the treatment of cancer, particularly to combinations of nitroxoline, or its analogues or pharmaceutically acceptable salts thereof, with at least one additional anti-cancer chemotherapy or immunotherapy agent, wherein the combination therapy shows synergistic anti-cancer effects.

BACKGROUND OF THE INVENTION

Combination therapies for the treatment of cancers serve to minimize the chances of the cancer developing resistance to any one anti-cancer therapy, and they allow for the use of lower doses of the individual anti-cancer therapies, resulting in reduced toxicities. Depending on the nature of drug-drug interactions, the combination of two active ingredients may result in a synergistic effect, additive effect or antagonistic effect.

Nitroxoline (NIT) is an antimicrobial agent which has been commercially marketed for a long time for the treatment of urinary tract infections. It was recently discovered that nitroxoline is also active in inhibiting angiogenesis (4) and inhibiting the growth and invasion of cancer (5, 6). NIT and its analogues, such as oxyquinoline, clioquinol and iodoquinol, share a common clinical use in treating infectious diseases. NIT analogues were also reported to have anti-cancer cytotoxicities (7). However, to the knowledge of the inventors, none of these drugs have been investigated in combination with other anti-cancer drugs, and drug-drug interaction of NIT or its analogues with any of the other cancer therapies has not been reported.

There exists a need in the art for novel combination therapies to treat cancers with enhanced anti-cancer effects or reduced toxicities.

BRIEF SUMMARY OF THE INVENTION

The present invention satisfies these needs by providing novel combination therapies involving nitroxoline, its analogues or pharmaceutically acceptable salts thereof with at least one additional anti-cancer chemotherapy or immunotherapy agent. The combination therapies demonstrate synergistic effects on the inhibition of cancer cell growth.

In one general aspect, the present invention provides a method for treating cancer by administering to a subject in need thereof nitroxoline, its analogue, or a pharmaceutically acceptable salt thereof, in combination with a chemotherapy. The chemotherapy is preferably selected from the group consisting of a microtubule disassembly inhibitor, an agent that cross-links DNA, and a platinum compound.

In another general aspect, the present invention provides a method for treating cancer by administering to a subject in need thereof nitroxoline, its analogue, or a pharmaceutically acceptable salt thereof, in combination with an immunotherapy agent. The immunotherapy agent is preferably an agent that can stimulate an effective immune response and inhibit immune-suppression. More preferably, the immunotherapy agent is an inhibitor or modulator of regulatory T cells or myeloid-derived suppressor cells.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. For the purpose of illustrating the invention, they are shown in the drawings embodiments which are presently preferred. It should be understood, however, that the invention is not limited to the precise arrangements and instrumentalities shown. In the drawings:

FIG. 9 shows the inhibition of tumor growth by the combination of oral NIT and mitomycin C in an orthotopic mouse MBT-2-Luc bladder cancer model;

FIG. 11 shows the inhibition of tumor growth by the combination of oral NIT and anti-PD-1 antibody in an orthotopic mouse MBT-2-Luc bladder cancer model.

DETAILED DESCRIPTION OF THE INVENTION

Figure 1:
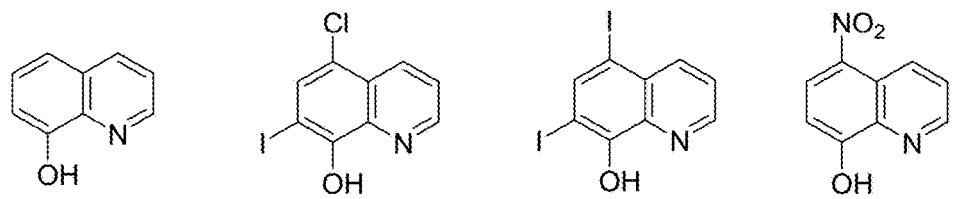
FIG. 1 shows the structures of nitroxoline (NIT) and examples of its analogues.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Definitions

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the terms "treat," "treating," and "treatment" are all intended to refer to an amelioration or reversal of at least one measurable physical parameter related to a cancer which is not necessarily discernible in the subject, but can be discernible in the subject. The terms "treat," "treating," and "treatment," can also refer to causing regression, preventing the progression, or at least slowing down the progression of the cancer. In a particular embodiment, "treat," "treating," and "treatment" refer to an alleviation, prevention of the development or onset, or reduction in the duration of one or more symptoms associated with the cancer. In a particular embodiment, "treat," "treating," and "treatment" refer to prevention of the recurrence of the cancer. In a particular embodiment, "treat," "treating," and "treatment" refer to an increase in the survival of a subject having the cancer. In a particular embodiment, "treat," "treating," and "treatment" refer to elimination of the cancer in the subject.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "effective amount" or "therapeutically effective amount" refers to an amount of an active ingredient or component that elicits the desired biological or medicinal response in a subject. In particular embodiments, the effective amount is the amount of an active ingredient or compound that is effective to achieve a synergistic effect with another active ingredient or compound. As used herein, a "synergistic effect" refers to an effect which is greater than the additive effect of the two individual active ingredients or compounds on the treatment of cancer. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. For example, drug combinations can be evaluated using a mathematical algorithm based on Loewe's model of additivity. In this model, combination index (CI) values are calculated. CI<1, CI=1, and CI>1 indicate synergistic, additive and antagonistic interactions, respectively.

As used herein, the term "pharmaceutically acceptable salt" refers to a salt form of nitroxoline or one of its analogues that is safe and effective. Non-limiting examples of pharmaceutically acceptable salts include: hydrochloride, hydrobromide, hydroiodide, sulfate, bisulfate, citrate, acetate, succinate, ascorbate, oxalate, nitrate, pears salts, hydrogen phosphate, dihydrogen phosphate, salicylate, hydrogen citrate, tartrate, maleate, fumarate, formate, benzoate, methanesulfonate, ethanesulfonate, benzenesulfonate, and p-toluenesulfonate. Preferably, a pharmaceutically acceptable salt of nitroxoline is a base addition salt of nitroxoline, such as those described in International Patent Application No. PCT/US14/30532, the entire content of which is incorporated herein by reference.

As used herein, the term "chemotherapy agent" refers to any chemical substance that is an anti-cancer drug.

As used herein, the term "immunologic agent" or "immunologic modulator" refers to any agent that is capable of stimulating an immune response and/or inhibiting immune-suppression.

As used herein, the term "in combination," in the context of the administration of two or more therapies to a subject, refers to the use of more than one therapy. The use of the term "in combination" does not restrict the order in which therapies are administered to a subject. For example, a first therapy (e.g., an effective amount of nitroxoline, or an analogue or pharmaceutically acceptable salt thereof described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., an effective amount of an immunotherapy agent or an effective amount of a chemotherapeutic agent) to a subject.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a nitroxoline-based pharmaceutical composition can be used in the invention. Non-limiting examples of carriers include saline and water.

Nitroxoline (NIT) and its Analogues

As shown in FIG. 1, NIT and its analogues, such as oxyquinoline, clioquinol and iodoquinol, share a common clinical use in treating infectious diseases. NIT is a broad-spectrum antibiotic, and it has been marketed to treat urinary tract infections since the 1960s. Its mechanism of action in inhibiting bacterial growth remains uncharacterized. NIT was found to inhibit adherence of uropathogenic *E. coli* to uroepithelial cells and urinary catheters at sub-MICs of NIT, and it is thought that NIT promotes disorganization of the bacterial outer membrane by chelating the divalent ions $Mg^{2+}$ and $Mn^{2+}$ (1). Oxyquinoline (Oxine) is an antiseptic with mild fungistatic, bacteriostatic, anthelmintic, and amebicidal activities. Oxine is capable of inhibiting isolated *E. coli* RNA polymerase without directly contacting the enzyme by essentially depriving the enzyme of $Mn^{2+}$ and $Mg^{2+}$ (2). Oxine is also used as a metal chelating agent, and so as a carrier for radio-indium for diagnostic purposes. Clioquinol has long been used as a topical anti-infective, intestinal antiamebic, and vaginal trichomonacide. The oral preparation of clioquinol has been shown to cause subacute myelo-optic neuropathy and has thus been banned worldwide. Clioquinol was found to halt cognitive decline in Alzheimer's disease in animal models, possibly due to its ability to act as a chelator of $Cu^{2+}$ and $Zn^{2+}$ (3). Iodoquinol is another halogenated 8-quinolinol widely used as an intestinal antiseptic, especially as an antiamebic agent. It is also used topically for other infections and may cause CNS and eye damage. Its mechanism of action remains unknown.

NIT and its analogues have been shown to have anti-cancer activities. It was shown that NIT is a MetAP2 inhibitor and can therefore block cancer angiogenesis by inhibiting proliferation of human umbilical vein endothelial cells (HUVECs) (4). NIT was also shown to be able to induce apoptosis of prostate cancer cells (5), and its cytotoxicity against cancer cells was more pronounced when administered in combination with $Cu^{2+}$ (6). NIT analogues, such as clioquinol, oxine and iodoquinol, were also reported to have anti-cancer cytotoxicities (7).

Chemotherapies

Cancer is the uncontrolled growth of cells coupled with malignant behavior including invasion and metastasis, among other features. It is caused by the interaction between genetic susceptibility and environmental factors. These factors lead to accumulations of genetic mutations in oncogenes, genes that control the growth rate of cells, and tumor suppressor genes, genes that help to prevent cancer, giving cancer cells their malignant characteristics, such as uncontrolled growth. Chemotherapy is a category of cancer treatment that uses chemical substances, especially one or more anti-cancer drugs. In the broad sense, most chemotherapeutic drugs work by impairing mitosis (cell division), effectively targeting fast-dividing cells. As these drugs cause damage to cells, they are termed cytotoxic. Anti-cancer drugs prevent mitosis by various mechanisms including damaging DNA and inhibition of the cellular machinery involved in cell division. One theory as to why these drugs kill cancer cells is that they induce a programmed form of cell death known as apoptosis. There are many types of cytotoxic chemotherapies in clinical use for treating cancer, and they are grouped into different classes according to the chemical structural characteristics. See, for example, Table 1 below.

TABLE 1

List of anti-cancer chemotherapies

| Class | Mechanism of Action | Drug Names |
|---|---|---|
| Nucleoside analogues | DNA methyltransferase inhibitor and incorporates itself into RNA, hence inhibiting gene expression | azacitidine, cladribine, decitabine, floxuridine |
| | thymidylate synthase inhibitor | capecitabine, carmofur, fluorouracil, tegafur |
| | ribonucleotide reductase and DNA polymerase inhibitor | clofarabine |
| | DNA polymerase inhibitor, S-phase specific; incorporates its metabolites into DNA | cytarabine, fludarabine |
| | DNA synthesis inhibitor, induces apoptosis specifically in S-phase | gemcitabine |
| | purine synthesis inhibitor | mercaptopurine, nelarabine, tioguanine |
| | adenosine deaminase inhibitor | pentostatin |
| Anti-metabolites | dihydrofolate reductase inhibitors | methotrexate, pemetrexed, pralatrexate, raltitrexed |
| | Inhibits DNA synthesis by inhibiting the enzyme ribonucleotide reductase | hydroxycarbamide |
| Topoisomerase I inhibitors | topoisomerase inhibitors | irinotecan, topotecan |
| Anthracyclines | inhibits DNA and RNA synthesis by intercalating DNA base pairs; inhibits DNA repair by inhibiting topoisomerase II | daunorubicin, doxorubicin, epirubicin, idarubicin, mitoxantrone, valrubicin |
| Podophyllo-toxins | topoisomerase II inhibitor | etoposide, teniposide |
| Taxanes | Microtubule disassembly inhibitor. Arrests cells in late G2 phase and M phase. | cabazitaxel, docetaxel, paclitaxel, and taxanes mixed or conjugated with proteins or antibodies |
| Vinca alkaloids | microtubule assembly inhibitor, arrests cells in M phase | vinblastine, vincristine, vindesine, vinflunine, vinorelbine |
| Alkylating agents | alkylates DNA | bendamustine, busulfan, carmustine, chlorambucil, chlormethine, cyclophosphamide, dacarbazine, Fotemustine, Ifosfamide, lomustine, melphalan, streptozotocin, temozolomide, trabectedin |
| Platinum compounds | reacts with DNA, inducing apoptosis, non-cell cycle specific | carboplatin, cisplatin, nedaplatin, oxaliplatin |
| Miscellaneous others | unclear, reactive intermediates covalently bind to microsomal proteins and DNA, possibly causing DNA damage | altretamine |
| | inhibits DNA and to a lesser extent RNA synthesis, produces single and double strand breaks in DNA possibly by free radical formation | bleomycin |
| | proteasome inhibitor | bortezomib, carfilzomib |
| | complexes with DNA interfering with DNA-dependent RNA synthesis | dactinomycin |

TABLE 1-continued

List of anti-cancer chemotherapies

| Class | Mechanism of Action | Drug Names |
|---|---|---|
| | antimicrotubule and estrogenic actions | estramustine |
| | promotes tubulin polymerisation and stabilises microtubular function, causing cell cycle arrest at G2/M phase and subsequently induces apoptosis | ixabepilone |
| | cross-links DNA | mitomycin C |
| | inhibits DNA, RNA and protein synthesis | procarbazine |

Traditional chemotherapeutic agents are cytotoxic, and they act by killing cells that divide rapidly, which is one of the fundamental properties of most cancer cells. This targeting of rapidly-dividing cells means that chemotherapy also harms cells that divide rapidly under normal circumstances, such as cells in the bone marrow, the digestive tract, and in hair follicles, resulting in the most common side-effects of chemotherapy, including myelosuppression (decreased production of blood cells, hence also immunosuppression), mucositis (inflammation of the lining of the digestive tract), and alopecia (hair loss). Combination therapy involves treating a patient with a number of different drugs simultaneously. Because the drugs differ in their mechanism and side-effects, a combination therapy may minimize the chances of resistance developing to any one agent, thus can be used to treat resistant cancers or at lower doses to reduce toxicity. However, because of the unpredictable nature of drug-drug interactions, a combination of known treatments may also result in reduced efficacy or increased side effects.

Cancer Immunotherapies

Cancer immunotherapy attempts to stimulate the immune system to reject and destroy tumors. Tumors have been found to be able to escape host immunity by manipulating the tumor microenvironment and driving immunosuppression, such that although the components necessary for mounting an effective anti-tumor immune response are present in patients with cancer, the host usually fails to arrest tumor progression (8). Numerous molecular and cellular mechanisms have been proposed in the past to explain this counterintuitive scenario, largely focusing on the "immune escape" of tumors and suggesting that tumors develop the capability to avoid tumor-specific immune responses generated by the host, or they altogether disable the host anti-tumor immunity. This process, referred to as "tumor-induced immune suppression" has been recognized in recent years and is being intensively investigated. It appears that tumors can interfere with all components of the immune system, affecting all stages of the anti-tumor immune response.

Molecular alterations that occur in tumor cells as the tumor progresses from the pre-malignant to metastatic phenotype are a result of genetic instability, now recognized as a principal characteristic of all tumors. Genetic changes are detectable during early stages of tumorigenesis, become more pronounced as the tumor progresses, are the greatest in metastatic cells and are responsible for tumor heterogeneity and alterations in the antigenic epitope profile of tumor cells. It has been suggested that the immune system might drive these antigenic changes via "immune editing" by eliminating those malignant cells that are sensitive to immune intervention and allowing for the selection and survival of immune-resistant variants. The net result of immune editing is that the tumor escapes from the host immune system. Regulatory T cells (Treg) and myeloid-derived suppressor cells (MDSC) are two types of cells used by the tumor to execute an immune escape. Protection of immune cells from the adverse effects of Treg, MDSC or inhibitory factors, and thus enhancement of their effector functions, can restore effective anti-tumor immunity in patients with cancer.

$CD4^+CD25^{high}FOXP3^+$ Treg cells accumulate in human tumors and in the peripheral circulation of patients with cancer. It is unclear whether these cells migrate to tumors or expand in situ. Because tumor-associated antigens (TAA) are self-antigens, it is possible that Treg accumulation is a response to enforce immune tolerance. Treg cells contribute to the down-regulation of immune activity of effector T cells by a variety of mechanisms including IL-10 and TGF-β1 production, enzymatic degradation of ATP to immunosuppressive adenosine, or the engagement of the Fas/FasL and granzyme/perforin pathways. Tumors benefit from immunosuppressive effects mediated by Treg.

Bone marrow-derived immature myeloid cells MDSC ($CD34^+CD33^+CD13^+CD15^-$) are present at an elevated frequency in the peripheral circulation and tumors of nearly all cancer patients. They are recruited by tumor-derived soluble factors such as TGF-01, IL-10, VEGF, GMCSF, IL-6, PGE2. They promote tumor growth by suppressing T-cell responses via several mechanisms, including production of arginase-1, an enzyme involved in L-arginine metabolism, as well as activation of inducible nitric oxide synthase (iNOS). They also control the tumor's production of indoleamine-2, 2-dioxygenase (IDO), which is involved in the catabolism of tryptophan, an amino acid essential for T-cell differentiation.

Bacillus Calmette-Guerin (BCG) immunotherapy for early stage (non-invasive) bladder cancer utilizes instillation of attenuated live bacteria into the bladder, and is effective in preventing recurrence in up to two thirds of cases. The immune response to BCG can be summarized as follows (9): infection of urothelial and bladder tumor cells by BCG results in internalization of BCG, which increases the expression of antigen-presenting molecules. This induces an immune response via the release of cytokines, such as Th1 cytokines (IL-2, tumor necrosis factor, IL-12, and IFN-γ) and Th2 cytokines (IL-4, IL-5, IL-6, and IL-10) along with IL-8 and IL-17. This complex immune cascade induces antitumor activity mediated by cytotoxic T lymphocytes, natural killer cells, neutrophils, and macrophages. In another study of BCG in an orthotopic mouse bladder tumor model, the population of MDSCs was significantly downregulated following the high-dose BCG therapy compared with the low-dose therapy. In the same study, $CD4^+/Foxp3^+$ Tregs also exhibited the same change. Following the BCG treatment, the population of $CD4^+/Foxp3^+$ Tregs was decreased in the blood. These inhibitory effects on the immune-suppressive factors may explain the robust antitumor therapeutic effects of the BCG therapy (10).

Immune checkpoint regulators, which can be both costimulatory and coinhibitory molecules, regulate the immune system. The balance between these checkpoints signals regulates lymphocyte activation and consequently the immune response. Tumors can use these checkpoint regulators to protect themselves from the immune system. Immune checkpoint therapies can enhance the proliferation, migration, persistence, and/or cytotoxic activity of T cells in a subject and, in particular, by increasing the numbers of tumor infiltrating T cells (11). The best characterized immune checkpoint receptors are cytotoxic T-lymphocyte-associated antigen 4 (CTLA-4; also known as CD152), programmed cell death protein 1 (PD-1; also known as CD279), and indoleamine 2,3-dioxygenase (IDO), and agents targeting these molecules are either approved or being extensively tested in clinical trials for treatment of multiple solid or hematological cancers.

CTLA-4, an inhibitory receptor, is a global immune checkpoint regulator engaged in priming immune responses via down-regulating the initial stages of T-cell activation. CTLA-4 was the first clinically validated checkpoint pathway target. CTLA-4 is homologous to the T-cell costimulatory protein CD28, and both molecules bind to CD80 and CD86 on antigen-presenting cells. CTLA-4 binds CD80 and CD86 with a markedly higher affinity and avidity than CD28 does, enabling CTLA-4 to outcompete CD28 for its ligands, resulting in an effective inhibition of T cell activation (12). Blocking CTLA-4 activity by using an antagonistic antibody interferes with this mechanism and thus preserves the activity of the T cells. Currently, Bristol-Myers Squibb's anti-CTLA-4 mAb, ipilimumab, has received US Food and Drug Administration (FDA) approval for patients with metastatic melanoma. Additionally, AstraZeneca's anti-CTLA-4 mAb, tremelimumab, has been granted orphan drug designation by the FDA for the treatment of patients with malignant mesothelioma.

PD-1 is another inhibitory receptor expressed on activated T and B cells, and it functions to dampen the immune response (13). PD-1 acts as an immune checkpoint regulator, and upon binding of one of its ligands, PD-L1 (B7-H1, CD274) or PD-L2 (B7-DC, CD273), PD-1 inhibits proliferation and cytokine production of T cells. Overexpression of PD-L1 or PD-L2 in the tumor microenvironment leads to the inhibition of the intratumoral immune responses (14). Inhibition of the interaction between PD-1 and PD-L1 by anti-PD-1/PD-L1 antibodies can inhibit the deactivation of T cells, and thus enhance anti-tumor responses, delay tumor growth, and facilitate tumor rejection (15). Two anti-PD-1 mAbs, Bristol-Myers Squibb's nivolumab, and Merck's pembrolizumab, have received US FDA approval for patients with metastatic melanoma and non-small-cell lung cancer. Recently, the FDA approved nivolumab as a treatment for patients with metastatic renal cell carcinoma. In 2016, Roche's anti-PD-L1 mAb, atezolizumab, was approved by the FDA for treating metastatic urothelial cancer and non-small cell lung cancer. Other anti-PD-L1 mAbs, such as AstraZeneca's durvalumab and Pfizer's avelumab, are in late-stage clinical trials.

Indoleamine 2,3-dioxygenase (IDO) is an enzyme that catalyzes the oxidative cleavage of tryptophan (16). IDO plays a role in suppressing the immune system because T cells undergoing antigen-dependent activation require tryptophan for cell proliferation and survival (17). IDO is overexpressed in most tumors and/or tumor-draining lymph nodes and it plays a significant role in helping tumors to evade attack from the immune system. IDO inhibitors block the IDO enzyme which reduces the depletion of tryptophan and ultimately may help to promote an enhanced immune response against the tumor (18). Currently, a number of clinical trials are underway to evaluate IDO inhibitors for both monotherapy and combination cancer therapies.

In addition to PD-1, CTLA-4, and IDO, other immune checkpoints are also involved in the occurrence and development of malignant tumors, including T cell membrane protein-3 (TIM-3), LAG3, T-cell immunoreceptor with Ig and immunoreceptor tyrosine-based inhibitory motif (ITIM) domains (TIGIT), BTLA, inducible T-cell costimulator (ICOS), killer inhibitory receptors (KIR), and V-domain Ig-containing suppressor of T cell activation (VISTA). Similar to PD-1, CTLA-4 and IDO, these immune checkpoints inhibit lymphocyte activity and/or induce lymphocyte anergy, and thus are ideal targets for cancer immunotherapy. Blocking antibodies for these immune checkpoints have shown specific anti-tumor activities in animal models, and some are being tested in clinical trials.

Methods of Treatment

In some aspects, the invention involves methods of combination therapy with an effective amount of nitroxoline, or an analogue or pharmaceutically acceptable salt thereof, and an effective amount of at least one second agent including any chemotherapeutic agents or immunotherapy agents for treating various types of cancer. The present invention provides methods for combining an effective amount of nitroxoline, or an analogue or pharmaceutically acceptable salt thereof, with an effective amount of an immunotherapy agent or a chemotherapeutic agent to produce significant enhancement of the anti-cancer effect, which is preferably synergistic.

The cancer can be any cancer. In some embodiments, the cancer is melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, glioblastoma, retinoblastoma, or hepatocellular carcinoma. In particular embodiments, the cancer is bladder cancer, prostate cancer, kidney cancer, urothelial carcinoma, testicular cancer, non-small cell lung cancer, breast cancer, or hepatocellular carcinoma. In more particular embodiments, the cancer is bladder cancer, prostate cancer, kidney cancer or urothelial carcinoma. In more particular embodiments, the cancer is bladder cancer or prostate cancer.

The second agent can be any chemotherapeutic agent that enhances the anti-cancer effect of nitroxoline, or an analogue or pharmaceutically acceptable salt thereof. In some embodiments, the second agent is a microtubule disassembly inhibitor, an agent that cross-links DNA, an agent that intercalates DNA base pairs, or a platinum compound. In some embodiments, the second agent is a microtubule disassembly inhibitor, such as a taxane, such as paclitaxel, docetaxel or cabazitaxel, or a taxane mixed or conjugated with proteins or antibodies. In some embodiments, the second agent is an agent that cross-links DNA, such as mitomycin C. In some embodiments, the second agent is an agent that intercalates DNA base pairs, such as an anthracycline, such as daunorubicin, doxorubicin, epirubicin, pirarubicin, idarubicin, mitoxantrone, or valrubicin. In some embodiments, the second agent is a platinum compound, such as carboplatin, cisplatin, nedaplatin or oxaliplatin. In particular embodiments, the second agent is selected from the group consisting of paclitaxel, mitomycin C, epirubicin, pirarubicin, cisplatin and carboplatin.

The second agent can also be any immunotherapy agent that enhances the anti-cancer effect of nitroxoline, or an analogue or pharmaceutically acceptable salt thereof. In some embodiments, the second agent is an immunologic agent that can stimulate an effective immune response and/or inhibit immune-suppression. In some embodiments, the second inhibitor is an agent that modulates, particularly inhibits and downregulates immune-suppressive factors such as regulatory T cells and MDSCs, including any inhibitors or antibodies of the programmed cell death 1 ligand 1 (PD-L1)/programmed cell death protein 1 (PD-1) pathway. In some embodiments, the second inhibitors are any effective inhibitors/antibodies capable of modulating immunocytes activities including but not limited to targeting cytotoxic T lymphocyte-associated antigen 4 (CTLA-4), CD20, CD19, IL-17a, CD25, arginase 1 (ARG1), indoleamine-2,3-dioxygenase (IDO), or tryptophan 2,3-dioxygenase (TDO2). In some embodiments, the second inhibitor is BCG. In particular embodiments, the second agent is an antibody against PD-1 or an antigen binding fragment thereof. In other particular embodiments, the second agent is an antibody against PD-L1 or an antigen binding fragment thereof. In other particular embodiments, the second agent is an antibody against CTLA-4 or an antigen binding fragment thereof. In other particular embodiments, the second agent is a BCG therapy, preferably an attenuated BCG therapy, more preferably mycobacterial cell wall fragments, and most preferably mycobacterial cell wall fragments with biologically active nucleic acids derived from *Mycobacterium phlei*.

The dosage of the compounds or agents are selected, e.g., based on required dose, fluid volumes, viscosities, etc., according to the particular mode of administration selected, to preferably achieve a synergistic effect. In some embodiments, the nitroxoline or its analogue or pharmaceutically acceptable salt thereof, is administered, preferably orally, in a dosage of about 100 mg/day to about 1600 mg/day, such as about 100 mg/day, 200 mg/day, 300 mg/day, 400 mg/day, 500 mg/day, 600 mg/day, 700 mg/day, 800 mg/day, 900 mg/day, 1000 mg/day, 1100 mg/day, 1200 mg/day, 1300 mg/day, 1400 mg/day, 1500 mg/day and 1600 mg/day. Preferably, the nitroxoline or its analogue or pharmaceutically acceptable salt thereof, is administered, preferably orally, in a dosage of about 600 mg/day to about 1600 mg/day.

In some embodiments, the second agent is an anti-PD-1 antibody or an antigen binding fragment thereof, preferably in a dosage of about 0.1 mg/kg to about 20 mg/kg, such as about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 mg/kg, administered, preferably by intravenous or intramuscular injection, once every 2, 3 or 4 weeks. More preferably, the anti-PD-1 antibody or antigen binding fragment thereof is administered, preferably by intravenous or intramuscular injection, in a total dosage of about 2 mg/kg to about 15 mg/kg in a period of about 3 weeks, and the treatment is optionally repeated one or more times.

In some embodiments, the second agent is an anti-PD-L1 antibody or an antigen binding fragment thereof, preferably in a dosage of about 1 mg/kg to about 40 mg/kg, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mg/kg, administered, preferably by intravenous or intramuscular injection, once every 2, 3 or 4 weeks. More preferably, the anti-PD-L1 antibody or antigen binding fragment thereof is administered, preferably by intravenous or intramuscular injection, in a total dosage of about 10 mg/kg to about 30 mg/kg in a period of 4 weeks, and the treatment is optionally repeated one or more times.

In some embodiments, the second agent is an anti-CTLA-4 antibody or an antigen binding fragment thereof, preferably in a dosage of about 0.1 mg/kg to about 6 mg/kg, such as about 0.1, 0.2, 0.3, 0.4, 0.5, 0.6, 0.7, 0.8, 0.9, 1, 2, 3, 4, 5 or 6 mg/kg administered, preferably by intravenous or intramuscular injection, once every 3, 4 or 5 weeks. More preferably, the anti-CTLA-4 antibody or antigen binding fragment thereof is administered, preferably by intravenous or intramuscular injection, in a total dosage of about 1 mg/kg to about 4 mg/kg in a period of about 4 weeks, and the treatment is optionally repeated one or more times.

In some embodiments, the second agent is a BCG therapy, preferably in a dosage of about $0.5 \times 10^8$ to about $50 \times 10^8$ colony forming units (CFUs), such as about 0.5×, 1×, 2×, 4×, 6×, 8×, 10×, 12×, 14×, 16×, 18×, 20×, 22×, 24×, 26×, 28×, 30×, 32×, 34×, 36×, 38×, 40×, 42×, 44×, 46×, 48× or $50 \times 10^8$ CFUs, administered, preferably intravesically, once every 1, 2, 3, 4, or 5 weeks. More preferably, the BCG therapy is administered, preferably intravesically, in a dose of about $1 \times 10^8$ to about $8 \times 10^8$ CFUs once a week, and the treatment is optionally repeated one or more times.

In some embodiments, the second agent is a chemotherapeutic agent administered, preferably intravesically, at a concentration of about 0.1 mg/ml or more, up to the agent's highest solubility in water or saline. In some embodiments, the chemotherapeutic agent is a DNA cross-linking or intercalating agent, such as mitomycin C, an anthracycline (e.g., epirubicin, pirarubicin, etc.), a platinum-based antineoplastic agents (e.g., carboplatin, cisplatin, oxaliplatin, nedaplatin), at a concentration of about 0.1 mg/ml to about 5 mg/ml, such as about 0.1, 0.5, 1, 1.5, 2, 2.5, 3, 3.5, 4, 4.5 or 5 mg/ml, administered, preferably intravesically, in a bladder instillation fluid, once every 1, 2, 3, 4 or 5 weeks. More preferably, the chemotherapeutic agent is administered, preferably intravesically, once a week at a concentration of about 0.5 mg/mL to 2 mg/mL in a bladder instillation fluid, and the treatment is optionally repeated one or more times.

In some embodiments, the chemotherapeutic agent is a taxane drug that targets tubulin, such as paclitaxel, docetaxel, cabazitaxel, a conjugate thereof with a protein or antibody, etc., at a concentration of about 0.5 mg/ml to about 10 mg/ml of the taxane drug, such as about 0.5, 1, 1.5, 2, 2.5, 3, 3.5, 4, 4.5, 5, 5.5., 6, 6.5, 7, 7.5, 8, 8.5, 9, 9.5 or 10 mg/ml, administered, preferably intravesically, in a bladder instillation fluid, once every 1, 2, 3, 4 or 5 weeks. More preferably, the taxane drug is administered, preferably intravesically, once a week at a concentration of about 1 mg/mL to 5 mg/mL in a bladder instillation fluid, and the treatment is optionally repeated one or more times.

The compounds or agents can be administered by any acceptable route. In some embodiments, the compounds are administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesically, intravitreally, liposomally, locally, mucosally, orally, parenterally, rectally, subconjunctival, subcutaneously, sublingually, topically, transbuccally, transdermally, vaginally, in creams, in lipid compositions, via a catheter, via a lavage, via continuous infusion, via infusion, via inhalation, via injection, via local delivery, via localized perfusion, bathing target cells directly, or any combination thereof. In some embodiments, the nitroxoline or its analogue or pharmaceutically acceptable salt thereof, is administered orally or by injections, and is preferably administered orally. In some embodiments, the immunotherapy agent is an antibody that is administered by injections. In some embodiments, the immunotherapy agent is a BCG therapy that is administered intravesically or by injections, and preferably is administered intravesically. In some embodiments, the chemotherapeutic agent is administered intravesically or by injections, and preferably is administered intravesically.

In some embodiments, the compounds or agents are administered once daily. In other embodiments, the compounds or agents are administered twice daily. In other embodiments, the compounds are administered multiple times a day, once every two days, once every three days, once every four days, once every five days, once every six days, once ever seven days, once every two weeks, once every three weeks, once every four weeks, once every two months, once every three months, once every four months, once every five months, once every six months, or once per year. The dosage regimen of the nitroxoline or its analogue, or a pharmaceutically acceptable salt thereof can be different from that of the immunotherapy agent or of the chemotherapeutic agent.

The compounds or agents can be administered for one day, two days, three days, four days, five days, six days, seven days, two weeks, three weeks, four weeks, two months, three months, four months, five months, six months, one year, two years three years, four years, five years, ten years, of fifteen years.

Methods of the present invention can be used in combination with additional cancer therapies. In some embodiments, the additional cancer therapy comprises surgery, radiotherapy, chemotherapy, toxin therapy, immunotherapy, cryotherapy or gene therapy. In some embodiments, the cancer is a chemotherapy-resistant, immunotherapy-resistant or radio-resistant cancer.

A combination treatment of the present invention according to embodiments of the invention can be achieved by way of the simultaneous, sequential or separate administration of the individual components of the treatment. A method of treatment in the present invention can be applied as the combination of an effective amount of nitroxoline, or an analogue or pharmaceutically acceptable salt thereof with an effective amount of an immunotherapy agent or an effective amount of a chemotherapeutic agent, in any animal model or in the clinic.

Compositions/Kits

Aspects of the invention also relate to a pharmaceutical composition or kit comprising an effective amount of nitroxoline or its analogue, or a pharmaceutically acceptable salt thereof, an effective amount of an immunotherapy agent or a chemotherapeutic agent, and a pharmaceutically acceptable carrier, as well as methods of manufacturing the pharmaceutical composition or kit by combining the nitroxoline or its analogues, or the pharmaceutically acceptable salts thereof, the at least one additional anti-cancer immunotherapy or chemotherapy agent, and a pharmaceutically acceptable carrier using methods known in the art in view of the present disclosure.

According to embodiments of the invention, a kit comprises one or more pharmaceutical compositions having an effective amount of nitroxoline, or an analogue or pharmaceutically acceptable salt thereof, and an effective amount of an immunotherapy agent. According to other embodiments of the invention, a kit comprises one or more pharmaceutical compositions having an effective amount of nitroxoline, or an analogue or pharmaceutically acceptable salt thereof, and an effective amount of a chemotherapeutic agent. The effective amount of nitroxoline, or an analogue or pharmaceutically acceptable salt thereof, and the effective amount of an immunotherapy agent or chemotherapeutic agent can be present in one pharmaceutical composition. They can also be present in separate pharmaceutical compositions. The kit further contains instructions on using the combination of the effective amount of nitroxoline, or an analogue or pharmaceutically acceptable salt thereof, and the effective amount of an immunotherapy agent or chemotherapeutic agent for treating a cancer.

Compositions or kits according to embodiments of the invention can be prepared using methods known in the art in view of the present disclosure.

According to particular embodiments, an effective amount refers to the amount of each active ingredient or compound that is effective to achieve a synergistic effect on one, two, three, four, or more of the following effects: (i) reduce or ameliorate the severity of the cancer to be treated or a symptom associated therewith; (ii) reduce the duration of the cancer to be treated, or a symptom associated therewith; (iii) prevent the progression of the cancer to be treated, or a symptom associated therewith; (iv) cause regression of the cancer to be treated, or a symptom associated therewith; (v) prevent the development or onset of the cancer to be treated, or a symptom associated therewith; (vi) prevent the recurrence of the cancer to be treated, or a symptom associated therewith; (vii) reduce hospitalization of a subject having the cancer to be treated, or a symptom associated therewith; (viii) reduce hospitalization length of a subject having the cancer to be treated, or a symptom associated therewith; (ix) increase the survival of a subject with the cancer to be treated, or a symptom associated therewith; (xi) inhibit or reduce the cancer to be treated, or a symptom associated therewith in a subject; and/or (xii) enhance or improve the prophylactic or therapeutic effect(s) of another therapy.

Embodiments

Embodiment 1 is a method of treating a cancer comprising administering to a subject in need thereof an effective amount of nitroxoline, or an analogue or pharmaceutically acceptable salt thereof, and an effective amount of an immunotherapy agent, preferably the immunotherapy agent is an inhibitor or modulator of regulatory T cells or myeloid-derived suppressor cells, and the combination of nitroxoline or the analogue or pharmaceutically acceptable salt thereof and the immunotherapy agent results in a synergistic effect.

Embodiment 2 is the method of Embodiment 1, wherein the immunotherapy agent is an inhibitor of the PD-L1/PD-1 pathway or an inhibitor of the CTLA-4 pathway, preferably the immunotherapy agent is an anti-PD-1 antibody, an anti-PD-L1 antibody, an anti-CTLA-4 antibody, or an antigen binding fragment thereof, more preferably, the antibody or fragment thereof is administered by intravenous or intramuscular injection.

Embodiment 3 is the method of Embodiment 1, wherein the immunotherapy agent is a *Bacillus* Calmette-Guerin (BCG) therapy, preferably an attenuated BCG therapy, more preferably mycobacterial cell wall fragments, and most preferably mycobacterial cell wall fragments with biologically active nucleic acids derived from *Mycobacterium phlei*, more preferably, the BCG therapy is administered intravesically.

Embodiment 4 is the method of Embodiment 3, wherein nitroxoline, the analogue or the pharmaceutically acceptable salt thereof is not administered within 24 hours of the intravesical instillation of the BCG therapy.

Embodiment 5 is the method of any one of Embodiments 1 to 4, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, glioblastoma, retinoblastoma, and hepatocellular carcinoma.

Embodiment 6 is the method of Embodiment 5, wherein the cancer is bladder cancer.

Embodiment 7 is the method of Embodiment 5, wherein the cancer is prostate cancer.

Embodiment 8 is the method of any one of Embodiments 1 to 7, wherein the effective amount of nitroxoline, or the analogue or pharmaceutically acceptable salt thereof is administered orally or by intravenous or intramuscular injection.

Embodiment 9 is a method of treating a cancer, preferably a bladder cancer, a liver cancer, or prostate cancer, comprising administering to a subject in need thereof an effective amount of nitroxoline or an analogue or pharmaceutically acceptable salt thereof, and an effective amount of a chemotherapeutic agent, wherein the combination of nitroxoline or the analogue or pharmaceutically acceptable salt thereof and the chemotherapeutic agent results in a synergistic effect.

Embodiment 10 is the method of Embodiment 9, wherein the chemotherapeutic agent is a taxane drug that targets tubulin, preferably paclitaxel, docetaxel, cabazitaxel; or the chemotherapeutic agent is DNA cross-linking or intercalating agent, preferably mitomycin C, an anthracycline that is preferably epirubicin, pirarubicin, or a platinum-based antineoplastic agent that is preferably carboplatin, cisplatin, oxaliplatin or nedaplatin.

Embodiment 11 is the method of Embodiment 9 or 10, wherein the chemotherapeutic agent is administered intravesically once every week, or once every 2, 3, 4 or 5 weeks.

Embodiment 12 is the method of any one of Embodiments 1 to 11, wherein the nitroxoline analogue is selected from the group consisting of oxyquinoline, clioquinol and iodoquinol.

Embodiment 13 is the method of any one of Embodiments 1 to 12, wherein the effective amount of nitroxoline or the analogue or pharmaceutically acceptable salt thereof is 100 mg to 1600 mg orally administered per day, preferably 600 mg to 1600 mg orally administered per day.

Embodiment 14 is a method of treating a cancer, preferably a bladder cancer or a prostate cancer, comprising administering to a subject in need thereof an effective amount of nitroxoline, or an analogue or pharmaceutically acceptable salt thereof, and an effective amount of an anti-PD-1 antibody or an antigen binding fragment thereof, wherein nitroxoline or the analogue or pharmaceutically acceptable salt thereof is orally administered 100 mg to 1600 mg per day, preferably 600 mg to 1600 mg per day, and the anti-PD-1 antibody or antigen binding fragment thereof is administered by intravenous or intramuscular injection 0.1 mg/kg to 20 mg/kg once every 1 to 4 weeks, preferably 2 mg/kg to 15 mg/kg in total in a period of 3 weeks, and the combination of nitroxoline or the analogue or pharmaceutically acceptable salt thereof and the anti-PD-1 antibody or antigen binding fragment thereof results in a synergistic effect.

Embodiment 15 is a method of treating a cancer, preferably a bladder cancer or a prostate cancer, comprising administering to a subject in need thereof an effective amount of nitroxoline, or an analogue or pharmaceutically acceptable salt thereof, and an effective amount of an anti-PD-L1 antibody or an antigen binding fragment thereof, wherein nitroxoline or the analogue or pharmaceutically acceptable salt thereof is orally administered 100 mg to 1600 mg per day, preferably 600 mg to 1600 mg per day, and the anti-PD-L1 antibody or antigen binding fragment thereof is administered by intravenous or intramuscular injection 1 mg/kg to 40 mg/kg once every 2 to 4 weeks, preferably 10 mg/kg to 30 mg/kg in total in a period of 4 weeks, and the combination of nitroxoline or the analogue or pharmaceutically acceptable salt thereof and the anti-PD-L1 antibody or antigen binding fragment thereof results in a synergistic effect.

Embodiment 16 is a method of treating a cancer, preferably a bladder cancer or a prostate cancer, comprising administering to a subject in need thereof an effective amount of nitroxoline, or an analogue or pharmaceutically acceptable salt thereof, and an effective amount of an anti-CTLA-4 antibody or an antigen binding fragment thereof, wherein nitroxoline or the analogue or pharmaceutically acceptable salt thereof is orally administered 100 mg to 1600 mg per day, preferably 600 mg to 1600 mg per day, and the anti-CTLA-4 antibody or antigen binding fragment thereof is administered by intravenous or intramuscular injection 0.1 mg/kg to about 6 mg/kg once every 3 to 5 weeks, preferably 1 mg/kg to 4 mg/kg in total in a period of 4 weeks, and the combination of nitroxoline or the analogue or pharmaceutically acceptable salt thereof and the anti-CTLA-4 antibody or antigen binding fragment thereof results in a synergistic effect.

Embodiment 17 is a method of treating a cancer, preferably a bladder cancer or a prostate cancer, comprising administering to a subject in need thereof an effective amount of nitroxoline, or an analogue or pharmaceutically acceptable salt thereof, and an effective amount of a BCG therapy, wherein nitroxoline or the analogue or pharmaceutically acceptable salt thereof is orally administered 100 mg to 1600 mg per day, preferably 600 mg to 1600 mg per day, and the BCG therapy is intravesically administered in a dosage of $0.5 \times 10^8$ to $50 \times 10^8$ colony forming units (CFUs) once every 1 to 5 weeks, preferably $1 \times 10^8$ to $8 \times 10^8$ CFUs once a week, and the combination of nitroxoline or the analogue or pharmaceutically acceptable salt thereof and the BCG therapy results in a synergistic effect.

Embodiment 18 is a method of treating a cancer, preferably a bladder cancer, a liver cancer or a prostate cancer, comprising administering to a subject in need thereof an effective amount of nitroxoline, or an analogue or pharmaceutically acceptable salt thereof, and an effective amount of a chemotherapeutic agent, wherein nitroxoline or the analogue or pharmaceutically acceptable salt thereof is orally administered 100 mg to 1600 mg per day, preferably 600 mg to 1600 mg per day, the effective amount of the chemotherapeutic agent is administered intravesically or by intravenous or intramuscular injection, and the combination of nitroxoline or the analogue or pharmaceutically acceptable salt thereof and the chemotherapeutic agent results in a synergistic effect.

Embodiment 19 is the method of Embodiment 18, wherein the chemotherapeutic agent is a DNA cross-linking or intercalating agent selected from the group consisting of mitomycin C, epirubicin, pirarubicin, carboplatin, cisplatin, oxaliplatin and nedaplatin, and the chemotherapeutic agent is administered intravesically once every 1-5 weeks in a bladder instillation fluid at a concentration of 0.1 mg/ml to 5 mg/ml, preferably 0.5 mg/mL to 2 mg/mL.

Embodiment 20 is the method of Embodiment 18, wherein the chemotherapeutic agent is a taxne drug selected from the group consisting of paclitaxel docetaxel and cabazitaxel, and the chemotherapeutic agent is administered intravesically in a bladder instillation fluid at a concentration of 0.5 to 10 mg/mL, preferably 1 to 5 mg/mL.

Embodiment 21 is the method of any one of Embodiments 1 to 20, wherein nitroxoline or a pharmaceutically acceptable salt thereof is administered orally or by injection to the subject in need thereof.

Embodiment 22 is the method of any one of Embodiments 1 to 20, wherein a nitroxoline analogue selected from the group consisting of oxyquinoline, clioquinol and iodoquinol or a pharmaceutically acceptable salt thereof is administered orally or by injection to the subject in need thereof.

Embodiment 23 is a kit comprising an effective amount of nitroxoline or its analogue, or a pharmaceutically acceptable salt thereof, an effective amount of an immunotherapy agent or chemotherapeutic agent, and one or more pharmaceutically acceptable carriers, wherein the effective amount of nitroxoline or the analogue or pharmaceutically acceptable salt thereof and the effective amount of the immunotherapy agent or chemotherapeutic agent are present in the same pharmaceutical composition or separate pharmaceutical compositions.

Embodiment 24 is the kit of Embodiment 23, wherein the kit comprises a pharmaceutical composition containing 100 mg and 1600 mg, preferably 600 mg to 1600 mg, per dosage form of nitroxoline or its analogue, or a pharmaceutically acceptable salt thereof.

Embodiment 25 is the kit of Embodiment 23 or 24, wherein the kit comprises a pharmaceutical composition containing the immunotherapy agent selected from the group consisting of an anti-PD-1 antibody or an antigen binding fragment thereof; an anti-PD-L1 antibody or an antigen binding fragment thereof; an anti-CTLA-4 antibody or an antigen binding fragment thereof; and a BCG therapy.

Embodiment 26 is the kit of Embodiment 23 or 24, wherein the kit comprises a pharmaceutical composition containing the chemotherapeutic agent selected from the group consisting of mitomycin C, epirubicin, pirarubicin, carboplatin, cisplatin, oxaliplatin, nedaplatin, paclitaxel docetaxel and cabazitaxel.

Embodiment 27 is the kit of any one of Embodiments 23 to 26, wherein the kit comprises a pharmaceutical composition containing nitroxoline or a pharmaceutically acceptable salt thereof.

Embodiment 28 is the kit of any one of Embodiments 23 to 26, wherein the kit comprises a pharmaceutical composition containing a nitroxoline analogue selected from the group consisting of oxyquinoline, clioquinol and iodoquinol, or a pharmaceutically acceptable salt thereof.

Embodiment 29 is a method of manufacturing the kit of any one of Embodiments 23 to 28, comprising combining the nitroxoline, its analogue, or the pharmaceutically acceptable salt thereof, the immunotherapy agent or the chemotherapeutic agent, and the one or more pharmaceutically acceptable carriers in the kit.

Embodiment 30 is a method of manufacturing the kit of any one of Embodiments 23 to 28, comprising obtaining a first pharmaceutical composition comprising the effective amount of nitroxoline, its analogue, or the pharmaceutically acceptable salt thereof, obtaining a second pharmaceutical composition comprising the effective amount of the immunotherapy agent or the chemotherapeutic agent, and combining the first and second pharmaceutical compositions in the kit.

Embodiment 31 is a use of a kit of any one of Embodiments 23 to 28 in the manufacture of a medicament for the treatment of cancer, and the combined use of nitroxoline or the analogue or pharmaceutically acceptable salt thereof and the immunotherapy agent or chemotherapeutic agent results in a synergistic effect.

Embodiment 32 is the use of Embodiment 31, wherein the cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, glioblastoma, retinoblastoma, and hepatocellular carcinoma.

Embodiment 33 is the use of Embodiment 32, wherein the cancer is bladder cancer.

Embodiment 34 is the use of Embodiment 32, wherein the cancer is prostate cancer.

Embodiment 35 is the use of Embodiment 32, wherein the cancer is liver cancer.

EXAMPLES

The following examples of the invention are to further illustrate the nature of the invention. It should be understood that the following examples do not limit the invention and that the scope of the invention is to be determined by the appended claims.

Example 1: Synergistic Inhibition of Tumor Growth by a Combination of NIT and One or More Chemotherapies NIT was tested with a group of chemotherapies including carboplatin, paclitaxel, mitomycin C, epirubicin and pirarubicin in the growth inhibition of two human cancer cell lines. As shown in Tables 2 and 3, NIT inhibited the growth of the human bladder cancer cell line 5637 and of the human liver cancer cell line HepG2.

TABLE 2

Incubation of NIT with the human bladder cancer cell line 5637 for 120 hours resulted in inhibition of cell growth.

| NIT (µg/ml) | OD Values | | | | Mean | SD | Inhibition Rates |
|---|---|---|---|---|---|---|---|
| 0 | 1.3 | 1.26 | 1.29 | 1.316 | 1.292 | 0.024 | |
| 0.25 | 1.148 | 1.126 | 0.798 | 1.164 | 1.059 | 0.175 | 18.0% |

TABLE 2-continued

Incubation of NIT with the human bladder cancer cell line 5637 for 120 hours resulted in inhibition of cell growth.

| NIT (μg/ml) | OD Values | | | | Mean | SD | Inhibition Rates |
|---|---|---|---|---|---|---|---|
| 0.5 | 0.606 | 0.624 | 0.632 | 0.618 | 0.620 | 0.011 | 52.0% |
| 1 | 0.254 | 0.268 | 0.25 | 0.264 | 0.259 | 0.008 | 79.9% |
| 2 | 0.097 | 0.104 | 0.098 | 0.097 | 0.099 | 0.003 | 92.3% |
| 4 | 0.056 | 0.06 | 0.058 | 0.056 | 0.058 | 0.002 | 95.5% |

TABLE 3

Incubation of NIT with the human liver cancer cell line HepG2 for 120 hours resulted in inhibition of cell growth.

| NIT(μg/ml) | OD Values | | | | Mean | SD | Inhibition Rates |
|---|---|---|---|---|---|---|---|
| 0 | 1.255 | 1.243 | 1.241 | 1.289 | 1.257 | 0.022 | |
| 0.5 | 1.264 | 1.195 | 1.243 | 1.164 | 1.217 | 0.045 | 3.2% |
| 1 | 0.975 | 1.046 | 0.977 | 0.939 | 0.984 | 0.045 | 21.7% |
| 2 | 0.273 | 0.255 | 0.245 | 0.217 | 0.248 | 0.023 | 80.3% |
| 4 | 0.113 | 0.124 | 0.124 | 0.118 | 0.120 | 0.005 | 90.5% |
| 8 | 0.086 | 0.082 | 0.08 | 0.081 | 0.082 | 0.003 | 93.5% |
| 16 | 0.057 | 0.06 | 0.061 | 0.06 | 0.060 | 0.002 | 95.3% |

As shown in Tables 4 and 5, carboplatin inhibited the growth of the human bladder cancer cell line 5637 and of the human liver cancer cell line HepG2.

TABLE 4

Incubation of carboplatin with the human bladder cancer cell line 5637 for 120 hours resulted in inhibition of cell growth.

| Carbo(μg/ml) | OD Values | | | | Mean | SD | Inhibition Rates |
|---|---|---|---|---|---|---|---|
| 0 | 1.3 | 1.26 | 1.29 | 1.316 | 1.292 | 0.024 | |
| 0.5 | 0.836 | 0.854 | 0.892 | 0.956 | 0.885 | 0.053 | 31.5% |
| 1 | 0.576 | 0.616 | 0.574 | 0.628 | 0.599 | 0.028 | 53.7% |
| 2 | 0.396 | 0.403 | 0.386 | 0.369 | 0.389 | 0.015 | 69.9% |
| 4 | 0.163 | 0.149 | 0.153 | 0.151 | 0.154 | 0.006 | 88.1% |
| 8 | 0.11 | 0.113 | 0.105 | 0.112 | 0.110 | 0.004 | 91.5% |

TABLE 5

Incubation of carboplatin with the human liver cancer cell line HepG2 for 120 hours resulted in inhibition of cell growth.

| Carbo (μg/ml) | OD Values | | | | Mean | SD | Inhibition Rates |
|---|---|---|---|---|---|---|---|
| 0 | 1.255 | 1.243 | 1.241 | 1.289 | 1.257 | 0.022 | |
| 4 | 0.761 | 0.747 | 0.767 | 0.796 | 0.768 | 0.021 | 38.9% |
| 8 | 0.361 | 0.308 | 0.346 | 0.328 | 0.336 | 0.023 | 70.7% |
| 16 | 0.148 | 0.177 | 0.18 | 0.175 | 0.170 | 0.015 | 85.2% |
| 32 | 0.104 | 0.125 | 0.133 | 0.136 | 0.125 | 0.014 | 89.1% |
| 64 | 0.08 | 0.083 | 0.084 | 0.076 | 0.081 | 0.004 | 93.0% |
| 128 | 0.074 | 0.068 | 0.068 | 0.068 | 0.070 | 0.003 | 93.9% |

As shown in Tables 6 and 7, paclitaxel inhibited the growth of the human bladder cancer cell line 5637 and of the human liver cancer cell line HepG2.

TABLE 6

Incubation of paclitaxel with the human bladder cancer cell line 5637 for 112 hours resulted in inhibition of cell growth.

| Taxol(ng/ml) | OD Values | | | | Mean | SD | Inhibition Rates |
|---|---|---|---|---|---|---|---|
| 0 | 1.028 | 1.023 | 0.987 | 0.988 | 1.007 | 0.022 | |
| 0.125 | 0.884 | 0.899 | 0.885 | 0.879 | 0.887 | 0.009 | 11.9% |
| 0.25 | 0.531 | 0.523 | 0.549 | 0.506 | 0.527 | 0.018 | 47.6% |
| 0.5 | 0.149 | 0.159 | 0.161 | 0.163 | 0.158 | 0.006 | 84.3% |
| 1 | 0.093 | 0.097 | 0.099 | 0.101 | 0.098 | 0.003 | 90.3% |
| 2 | 0.03 | 0.031 | 0.034 | 0.035 | 0.033 | 0.002 | 96.8% |

TABLE 7

Incubation of paclitaxel with the human liver cancer cell line HepG2 for 112 hours resulted in inhibition of cell growth.

| Taxol(ng/ml) | OD Values | | | | Mean | SD | Inhibition Rates |
|---|---|---|---|---|---|---|---|
| 0 | 1.79 | 1.764 | 1.73 | 1.845 | 1.782 | 0.049 | |
| 0.5 | 1.642 | 1.718 | 1.69 | 1.664 | 1.679 | 0.033 | 5.8% |
| 1 | 1.544 | 1.548 | 1.519 | 1.523 | 1.534 | 0.015 | 14.0% |
| 2 | 0.974 | 0.914 | 0.95 | 0.904 | 0.936 | 0.032 | 47.5% |
| 4 | 0.428 | 0.466 | 0.41 | 0.423 | 0.432 | 0.024 | 75.8% |
| 8 | 0.177 | 0.153 | 0.173 | 0.182 | 0.171 | 0.013 | 90.4% |
| 16 | 0.128 | 0.134 | 0.123 | 0.138 | 0.131 | 0.007 | 92.7% |

The $IC_{50}$ values of these compounds' inhibition of cell growth are summarized in Table 8.

TABLE 8

$IC_{50}$ values of NIT, carboplatin and paclitaxel for inhibition of cell growth of human bladder cancer cell line 5637 and of human liver cancer cell line HepG2.

| Cell Line | NIT (μg/ml) | Carboplatin (μg/ml) | Paclitaxel (ng/ml) |
|---|---|---|---|
| 5637 | 0.517 | 0.917 | 0.289 |
| HepG2 | 1.86 | 3.687 | 2.502 |

Mitomycin C, epirubicin and pirarubicin were similarly tested for inhibition of the growth of bladder cancer cell line 5637, and their $IC_{25}$, $IC_{50}$ and $IC_{75}$ values are summarized in Table 9.

TABLE 9

$IC_{25}$, $IC_{50}$ and $IC_{75}$ values of mitomycin C, epirubicin and pirarubicin for inhibition of cell growth of human bladder cancer cell line 5637.

| Drug | $IC_{25}$ (ng/ml) | $IC_{50}$ (ng/ml) | $IC_{75}$ (ng/ml) |
|---|---|---|---|
| Mitomycin C | 48.36 | 152.53 | 536.62 |
| Epirubicin | 34.97 | 45.21 | 63.93 |
| Pirarubicin | 96.58 | 142.57 | 219.58 |

Figure 2:
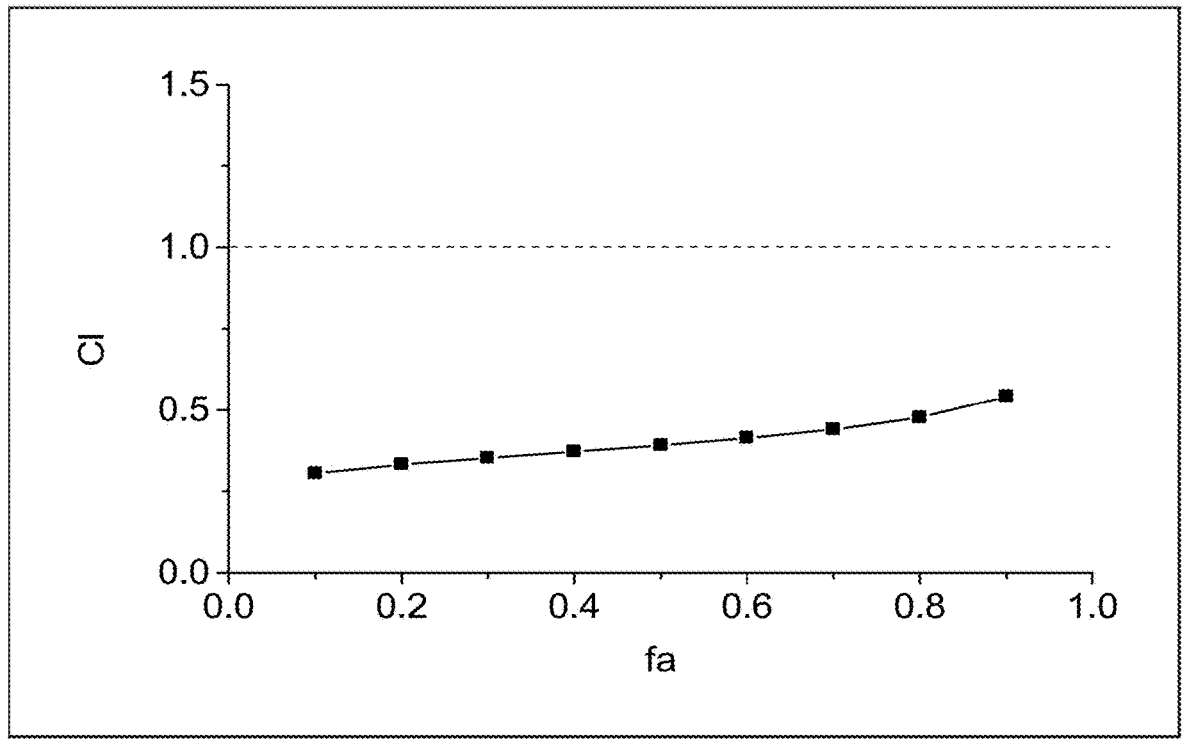
FIG. 2 shows combination index (CI) plots of the inhibition of the growth of human bladder cancer cell line 5637 by the combination of NIT and carboplatin.

The combinational studies of NIT and chemotherapies were conducted by mixing NIT with individual chemotherapies at five to seven concentration levels, with the medium concentration levels close to their $IC_{50}$ values. The combinational indices (CIs) were calculated and plotted according to Ting-Chao Chou's method (19) to estimate the combinational effects, including synergism, addition and antagonism. As shown in Tables 10 and 11, NIT inhibited the growth of human bladder cancer 5637 in combination with carboplatin and paclitaxel, respectively, and the CI values of the studies were calculated and plotted in FIGS. 2 and 3, respectively.

TABLE 10

Incubation of a combination of NIT and carboplatin with the human bladder cancer cell line 5637 for 120 hours resulted in inhibition of cell growth.

| NIT (µg/ml) | Carbo (µg/ml) | OD Values | | | | Mean | SD | Inhibition Rates |
|---|---|---|---|---|---|---|---|---|
| 0 | 0 | 1.324 | 1.364 | 1.296 | 1.348 | 1.333 | 0.030 | |
| 0.25 | 0.5 | 0.36 | 0.394 | 0.41 | 0.362 | 0.382 | 0.025 | 71.4% |
| 0.5 | 1 | 0.134 | 0.144 | 0.132 | 0.15 | 0.140 | 0.008 | 89.5% |
| 1 | 2 | 0.072 | 0.08 | 0.07 | 0.07 | 0.073 | 0.005 | 94.5% |
| 2 | 4 | 0.038 | 0.046 | 0.038 | 0.042 | 0.041 | 0.004 | 96.9% |
| 4 | 8 | 0.02 | 0.019 | 0.017 | 0.017 | 0.018 | 0.002 | 98.6% |

TABLE 11

Incubation of a combination of NIT and paclitaxel with the human bladder cancer cell line 5637 for 96 hours resulted in inhibition of cell growth.

| NIT (µg/ml) | Taxol (ng/ml) | OD Values | | | | Mean | SD | Inhibition Rates |
|---|---|---|---|---|---|---|---|---|
| 0 | 0 | 0.793 | 0.786 | 0.766 | 0.784 | 0.782 | 0.012 | |
| 0.125 | 0.125 | 0.567 | 0.536 | 0.542 | 0.516 | 0.540 | 0.021 | 30.9% |
| 0.25 | 0.25 | 0.375 | 0.42 | 0.385 | 0.424 | 0.401 | 0.025 | 48.7% |
| 0.5 | 0.5 | 0.082 | 0.083 | 0.081 | 0.086 | 0.083 | 0.002 | 89.4% |
| 1 | 1 | 0.027 | 0.03 | 0.026 | 0.027 | 0.028 | 0.002 | 96.5% |
| 2 | 2 | 0.015 | 0.014 | 0.013 | 0.015 | 0.014 | 0.001 | 98.2% |

Figure 4:
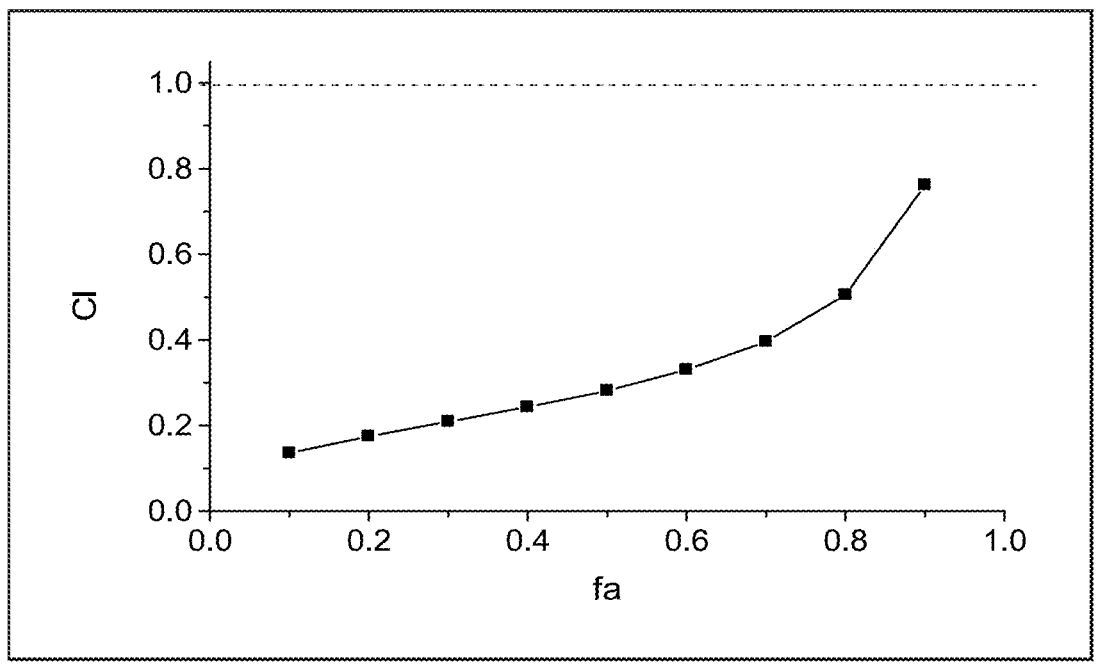
FIG. 4 shows CI plots of the inhibition of the growth of human liver cancer cell line HepG2 by the combination of NIT and carboplatin.
Figure 5:
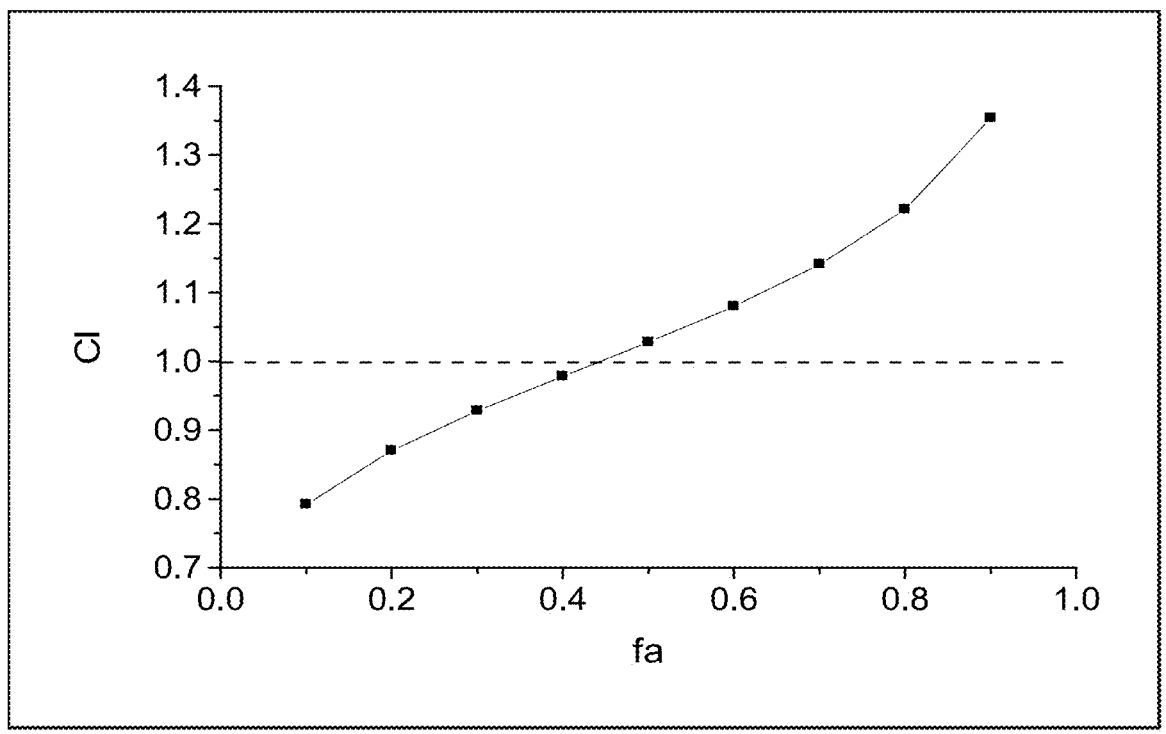
FIG. 5 shows CI plots of the inhibition of the growth of human liver cancer cell line HepG2 by the combination of NIT and paclitaxel.

As shown in Tables 12 and 13, NIT inhibited the growth of human liver cancer cell line HepG2 in combination with carboplatin and paclitaxel, respectively, the CI values of the studies are plotted in FIGS. 4 and 5, respectively.

TABLE 12

Incubation of a combination of NIT and carboplatin with the human liver cancer cell line HepG2 for 120 hours resulted in inhibition of cell growth.

| NIT (µg/ml) | Carbo (µg/ml) | OD Values | | | | Mean | SD | Inhibition Rates |
|---|---|---|---|---|---|---|---|---|
| 0 | 0 | 1.261 | 1.243 | 1.235 | 1.257 | 1.249 | 0.012 | |
| 0.5 | 4 | 0.469 | 0.496 | 0.472 | 0.454 | 0.473 | 0.017 | 62.1% |
| 1 | 8 | 0.133 | 0.134 | 0.138 | 0.146 | 0.138 | 0.006 | 89.0% |
| 2 | 16 | 0.098 | 0.094 | 0.093 | 0.097 | 0.096 | 0.002 | 92.4% |
| 4 | 32 | 0.077 | 0.08 | 0.079 | 0.081 | 0.079 | 0.002 | 93.7% |
| 8 | 64 | 0.051 | 0.05 | 0.049 | 0.052 | 0.051 | 0.001 | 96.0% |
| 16 | 128 | 0.047 | 0.043 | 0.046 | 0.043 | 0.045 | 0.002 | 96.4% |

TABLE 13

Incubation of a combination of NIT and paclitaxel with the human liver cancer cell line HepG2 for 120 hours resulted in inhibition of cell growth.

| NIT (µg/ml) | Taxol (ng/ml) | OD Values | | | | Mean | SD | Inhibition Rates |
|---|---|---|---|---|---|---|---|---|
| 0 | 0 | 1.393 | 1.397 | 1.451 | 1.414 | 1.414 | 0.026 | |
| 0.5 | 0.5 | 1.115 | 1.134 | 1.164 | 1.129 | 1.136 | 0.021 | 19.7% |
| 1 | 1 | 0.928 | 0.938 | 1.009 | 0.963 | 0.960 | 0.036 | 32.1% |
| 2 | 2 | 0.516 | 0.552 | 0.556 | 0.474 | 0.525 | 0.038 | 62.9% |
| 4 | 4 | 0.199 | 0.214 | 0.199 | 0.182 | 0.199 | 0.013 | 86.0% |
| 8 | 8 | 0.116 | 0.116 | 0.111 | 0.097 | 0.110 | 0.009 | 92.2% |
| 16 | 16 | 0.059 | 0.067 | 0.068 | 0.066 | 0.065 | 0.004 | 95.4% |

Figure 6:
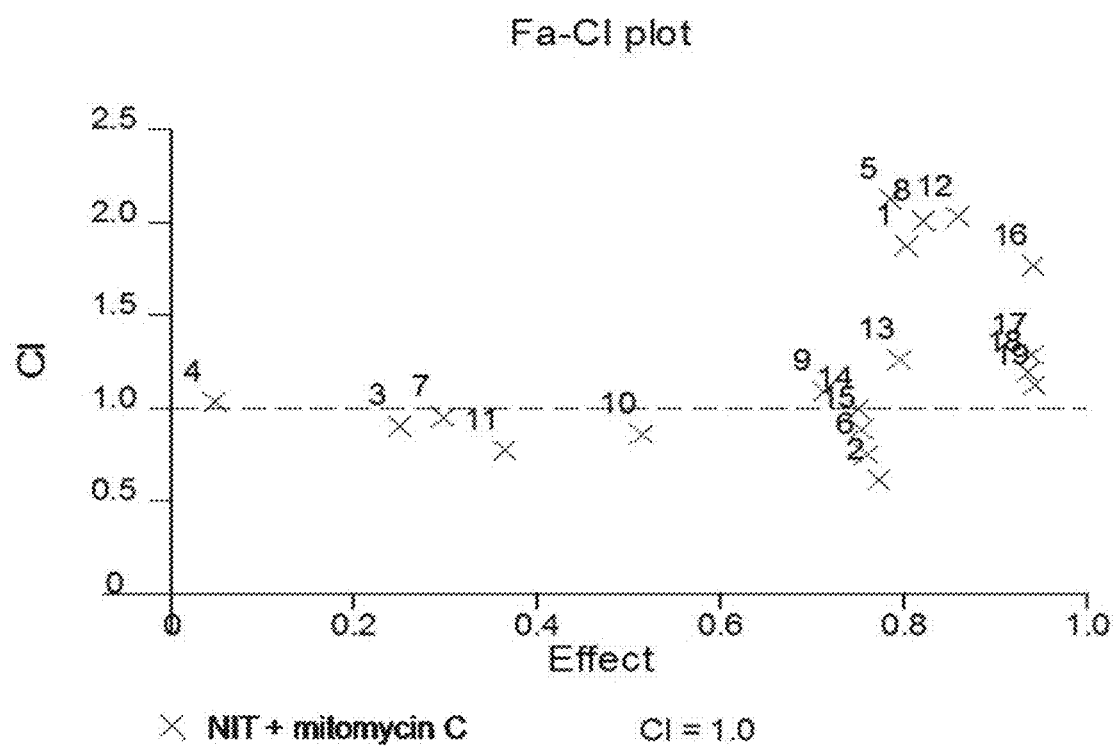
FIG. 6 shows CI plots of the inhibition of the growth of human bladder cancer cell line 5637 by the combination of NIT and mitomycin C.
Figure 7:
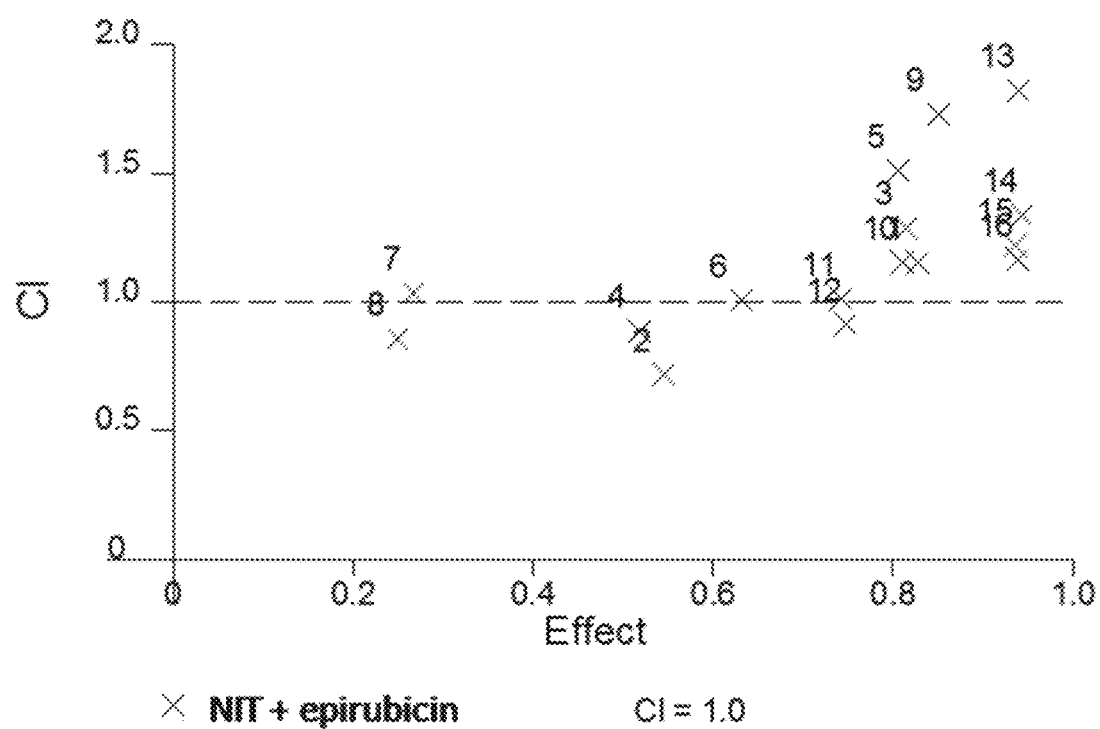
FIG. 7 shows CI plots of the inhibition of the growth of human bladder cancer cell line 5637 by the combination of NIT and epirubicin.
Figure 8:
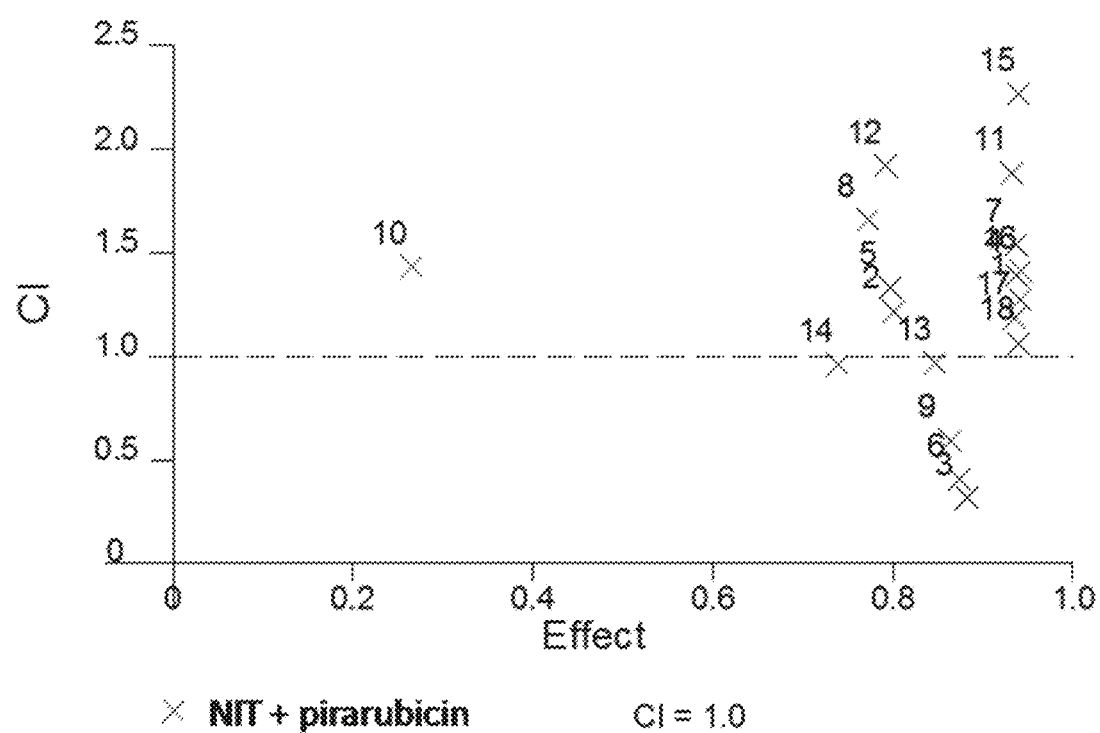
FIG. 8 shows CI plots of the inhibition of the growth of human bladder cancer cell line 5637 by the combination of NIT and pirarubicin.

Similarly, NIT was combined with mitomycin C, epirubicin and pirarubicin to inhibit the growth of bladder cancer cell line 5637, and their combinational inhibitory results and CI plots are shown in Tables 14-17 and FIGS. 6-8.

TABLE 14

Incubation of a combination of NIT and mitomycin C with the human bladder cancer cell line 5637 for 96 hours resulted in inhibition of cell growth.

| 5637 | Average Fa | NIT | | | | | |
|---|---|---|---|---|---|---|---|
| | | 10000 | 5000 | 2500 | 1250 | 625 | 0 |
| Mitomycin C | 200 | 94.1% | 85.9% | 82.1% | 78.6% | 80.3% | 79.4% |
| | 50 | 93.5% | 79.5% | 71.2% | 75.9% | 77.2% | 77.9% |
| | 12.5 | 93.5% | 75.0% | 51.4% | 29.7% | 24.9% | 27.7% |
| | 3.13 | 94.2% | 75.3% | 36.4% | 0.5% | 4.8% | 1.6% |
| | 0 | 94.0% | 74.3% | 23.3% | −3.8% | −7.2% | 0.0% |

TABLE 15

CI values of the combination of NIT and mitomycin C when incubated with the human bladder cancer cell line 5637 for 96 hours.

| | CI | NIT | | | | | |
|---|---|---|---|---|---|---|---|
| | | 10000 | 5000 | 2500 | 1250 | 625 | 0 |
| Mitomycin C | 200 | 1.764 | 2.032 | 2.011 | 2.122 | 1.874 | |
| | 50 | 1.289 | 1.263 | 1.094 | 0.749 | 0.613 | |
| | 12.5 | 1.194 | 0.996 | 0.861 | 0.952 | 0.905 | |
| | 3.13 | 1.126 | 0.888 | 0.772 | 5.148 | 1.033 | |
| | 0 | | | | | | |

TABLE 16

CI values of the combination of NIT and epirubicin when incubated with the human bladder cancer cell line 5637 for 96 hours.

| | | | NIT | | | |
|---|---|---|---|---|---|---|
| CI | 10000 | 5000 | 2500 | 1250 | 625 | 0 |
| Epirubicin 50 | 1.826 | 1.728 | 1.51 | 1.288 | 1.154 | |
| 16.67 | 1.339 | 1.158 | 1.009 | 0.885 | 0.718 | |
| 5.56 | 1.223 | 1.015 | 1.035 | 4.16 | 3.337 | |
| 1.85 | 1.166 | 0.914 | 0.857 | 2.483 | 1.66 | |
| 0 | | | | | | |

TABLE 17

CI values of the combination of NIT and pirarubicin when incubated with the human bladder cancer cell line 5637 for 96 hours.

| | | | NIT | | | |
|---|---|---|---|---|---|---|
| CI | 10000 | 5000 | 2500 | 1250 | 625 | 0 |
| pirarubicin 200 | 2.266 | 1.885 | 1.536 | 1.39 | 1.276 | |
| 66.67 | 1.405 | 1.915 | 1.664 | 1.333 | 1.219 | |
| 22.22 | 1.185 | 0.969 | 0.596 | 0.409 | 0.315 | |
| 7.41 | 1.067 | 0.965 | 1.437 | 5.521 | 11.846 | |
| 0 | | | | | | |

Figure 3:
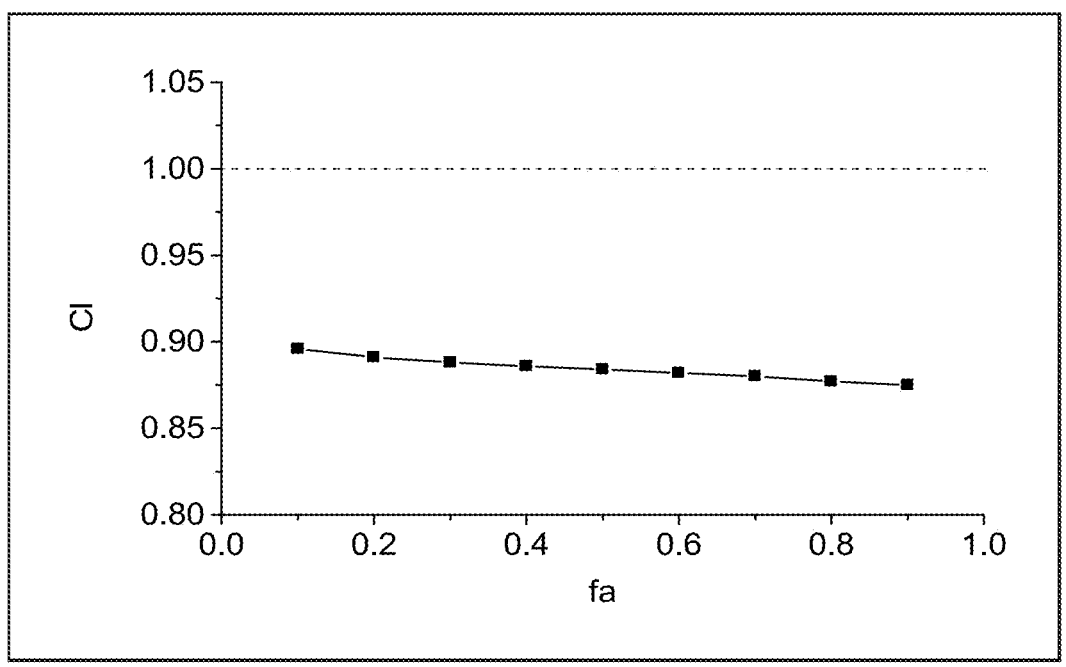
FIG. 3 shows CI plots of the inhibition of the growth of human bladder cancer cell line 5637 by the combination of NIT and paclitaxel.

According to Chou (19), a CI value below 0.9 represents a synergistic combination of the two drugs, and values of 0.1-0.3, 0.3-0.7, 0.7-085, and 0.85-0.9 represent strong synergism, synergism, moderate synergism and slight synergism, respectively. Therefore, the CI plots in FIGS. 2 and 4 support the conclusion that NIT and carboplatin inhibited the growth of the bladder cancer cell line 5637 and of the liver cancer cell line HepG2 in a manner that is classified as synergistic or strongly synergistic. The CI plot in FIG. 3 shows that the combination of NIT and paclitaxel demonstrated slight synergism in inhibiting the growth of the bladder cancer cell line 5637, and FIG. 5 shows that the inhibition of the growth of the liver cancer cell line HepG2 with this combination is partially synergistic when the drug concentrations' Fa (fraction absorbed) is lower than 0.3. This partial synergism at concentrations below the drugs' IC50 values was also found for the combination of NIT and mitomycin C for inhibition of the bladder cancer cell line 5637, as shown in Table 15 and FIG. 6. Tables 16 and 17 and FIGS. 7 and 8 showed that the combination of NIT with epirubicin or pirarubicin are partially synergistic at some concentrations for inhibition of the growth of the bladder cancer cell line 5637.

The synergistic tumor growth inhibition exhibited by NIT in combination with mitomycin C (MMC) was further evaluated in a mouse bladder cancer orthotopic xenograft. FIG. 9 shows the effect of combining orally dosed NIT and intravesically administered MMC on the inhibition of tumor development in a MBT-2-lucorthotopic mouse bladder cancer model. The tumor volume was analyzed by the Xenogen IVIS200 system following the indicated treatment. FIG. 9A shows a typical IVIS image for each treatment group. The tumor volume of each mouse was determined by region-of-interest analysis of total photons per second. Six mice were analyzed in each group. As shown in FIG. 9B, the mean tumor volume for the group of 15 mg/kg Bid oral NIT in combination with Q7d 1 mg/ml intravesical mitomycin C (NIT+MMC) was significantly different from that for single NIT or single MMC treatment groups (p<0.0001 and p=0.0001 respectively), indicating a remarkable enhancement in tumor growth inhibition by the combination treatment of NIT with MMC. The Kaplan-Meier analysis was also performed to assess mouse survival for each treatment and is summarized in FIG. 9C. Consistently, the survival status for the group of NIT plus MMC was significantly improved, in contrast to the control and single drug treatment groups.

The results of the tumor growth inhibition and survival proportions, as well as the Bliss independence model calculations of additivity are summarized in Table 18.

TABLE 18

Bliss independence model calculations of additivity for oral NIT in combination with MMC in an orthotopic mouse MBT-2-Luc bladder cancer model.

| | NIT + MMC | | | | |
|---|---|---|---|---|---|
| | Single drug | | Expected Bliss Additive Value | Actual Observed Value | Interaction |
| | NIT | MMC | | | |
| Tumor Growth Inhibition | 0.33 | 0.56 | 0.7 | 0.71 | Synergy |
| Survival Proportion | 0.33 | 0.57 | 0.71 | 1 | Synergy |

NIT administered orally at a dose of 15 mg/kg (Bid) inhibited tumor growth at a rate of 0.33, and the proportion of surviving mice at the end of the experiment (45 days) was 0.33. The tumor inhibition rate and the proportion of surviving mice for intravesically administered MMC treatment was 0.56 and 0.57 respectively. When oral NIT was dosed with MMC, the observed tumor inhibition rate and the proportion of surviving mice was significantly increased to 0.71 and 1, respectively, which were greater than their Expected Bliss Additive Values, indicating a synergy for tumor inhibition by the combination of NIT and MMC.

The discovery that NIT has different degrees of synergism with different classes of chemotherapies can be used for the combinational treatment of a variety of solid and blood tumors.

Example 2: Synergistic Inhibition of Tumor Growth by Combination of NIT with Immunotherapies NIT was tested with a group of immunotherapies including BCG and anti-PD-1 antibody for tumor growth inhibition of mouse bladder and prostate cancer orthotopic xenograft models.

Figure 10:
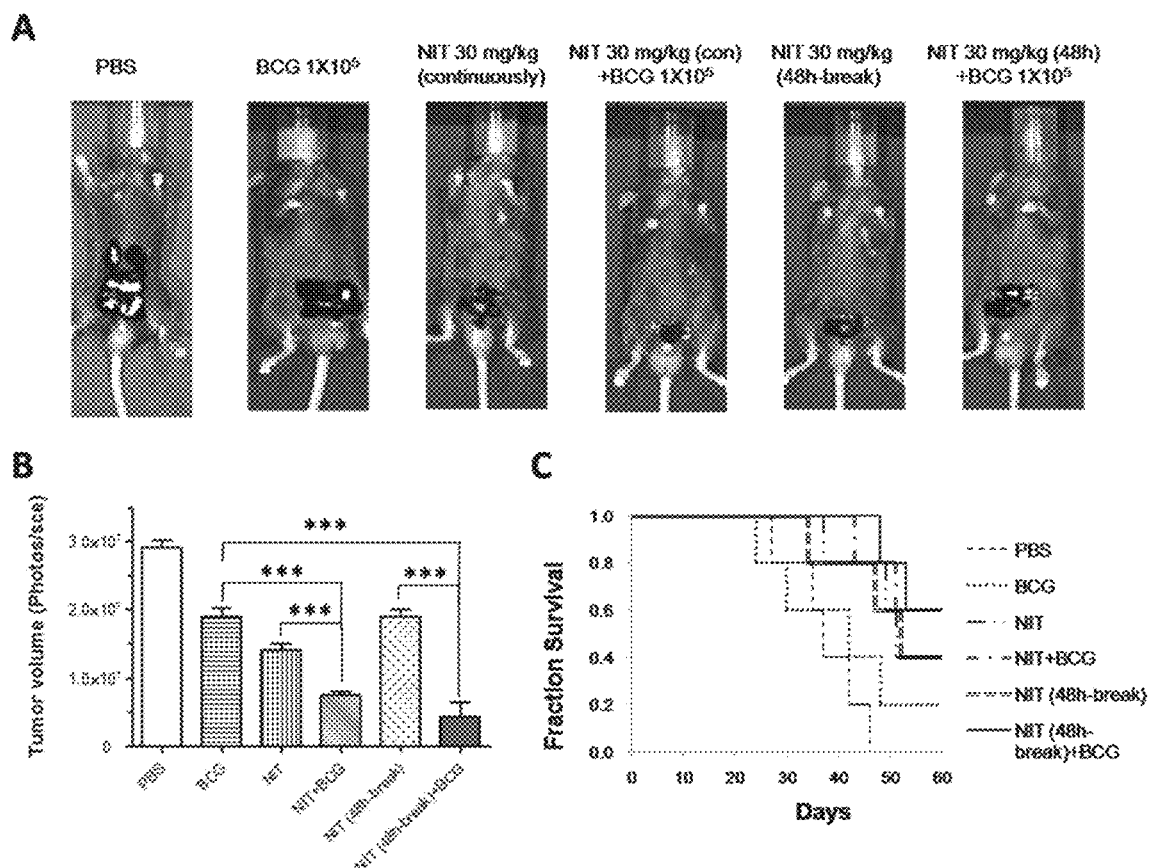
FIG. 10 shows the inhibition of tumor growth by the combination of oral NIT and intravesical BCG in an orthotopic mouse MBT-2-Luc bladder cancer model.

FIG. 10 shows the effect of combining orally dosed NIT and intravesically instilled BCG on inhibiting tumor development in a MBT-2-luc orthotopic mouse bladder cancer model. The tumor volume was analyzed by the Xenogen IVIS200 system following the indicated treatment, and a typical IVIS image for each treatment group of indicated treatment is shown in FIG. 10A. The tumor volume of each mouse was determined by region-of-interest analysis of total photons per second. Eight mice were analyzed in each group. As shown in FIG. 10B, 30 mg/kg NIT administered orally inhibited the cancer growth, either continuously or with a 48-hour break, at a slightly higher or similar activity compared to that caused by BCG administered intravesically. When oral NIT (administered continuously or with a 48-hour break) was dosed with BCG, the inhibition rates were significantly increased, compared to single NIT or BCG treatments (p<0.0001 for all comparisons). The Kaplan-Meier analysis was also performed to evaluate mouse survival for each treatment and is summarized in FIG. 10C. The survival status for the group of oral NIT (administered continuously or with a 48-hour break) in combination with BCG was significantly improved, compared to the single drug treatment groups.

The results of the Bliss independence model calculations of additivity for tumor growth inhibition and survival proportions are summarized in Table 19 (continuous NIT) and Table 20 (NIT with 48h break).

TABLE 19

Bliss independence model calculations of additivity for oral NIT (continuous) in combination with intravesical BCG in an orthotopic mouse MBT-2-Luc bladder cancer model.

|  | Single Drug | | NIT (continuous) + BCG | | |
|---|---|---|---|---|---|
|  | NIT (continuous) | BCG | Expected Bliss Additive Value | Actual Observed Value | Interaction |
| Tumor Growth Inhibition | 0.52 | 0.35 | 0.69 | 0.75 | Synergy |
| Survival Proportion | 0.4 | 0.2 | 0.52 | 0.60 | Synergy |

TABLE 20

Bliss independence model calculations of additivity for oral NIT (48 h-break) in combination with intravesical BCG in an orthotopic mouse MBT-2-Luc bladder cancer model.

|  | Single Drug | | NIT (48 h-break) + BCG | | |
|---|---|---|---|---|---|
|  | NIT (48 h-break) | BCG | Expected Bliss Additive Value | Actual Observed Value | Interaction |
| Tumor Growth Inhibition | 0.35 | 0.35 | 0.58 | 0.85 | Synergy |
| Survival Proportion | 0.4 | 0.2 | 0.52 | 0.60 | Synergy |

When oral NIT was administered in combination with intravesical BCG, either continuously or with a 48-hour break, the observed tumor inhibition rates and survival proportions were significantly increased, compared to that of single NIT and BCG treatments. The actual tumor inhibition rates and survival proportions of NIT in combination with BCG were much greater than their Expected Bliss Additive Value, suggesting a robust synergy in tumor inhibition by the combination of NIT and BCG.

To assess a synergistic tumor inhibition effect of NIT in combination with anti-PD-1, the combination was tested for tumor growth inhibition of mouse bladder and prostate cancer orthotopic xenograft models.

FIG. 11 shows the effect of orally dosed NIT combined with intraperitoneal anti-PD-1 antibody on inhibiting tumor growth in a MBT-2-luc orthotopic mouse bladder cancer model. Typical IVIS images for each indicated treatment group are shown in FIG. 11A. The tumor volume of each mouse was determined by region-of-interest analysis of total photons per second. Five mice were analyzed in each group. As shown in FIG. 11B, 10 mg/kg intraperitoneal anti-PD-1 intensively inhibited the tumor growth at a rate of 80%, while 15 mg/kg NIT administered orally showed a tumor inhibition rate of 31%. When oral NIT was combined with anti-PD-1, the inhibition rates were significantly enhanced (90%), compared to single NIT or anti-PD-1 treatments (p<0.0001 and p=0.039 respectively). The Kaplan-Meier analysis was also performed and is summarized in FIG. 11C. The survival status for the groups of NIT plus anti-PD-1 or the single anti-PD-1 was significantly higher than the single NIT group.

The results of the Bliss independence model calculations of additivity for tumor growth inhibition are summarized in Table 21. When NIT was administered in combination with anti-PD-1, its actual observed tumor inhibition rate was greater than the Expected Bliss Additive Value, suggesting a synergy in tumor inhibition.

TABLE 21

Bliss independence model calculations of additivity for oral NIT in combination with anti-PD-1 antibody in an orthotopic mouse MBT-2-Luc bladder cancer model.

|  | Single Drug | | NIT + anti-PD-1 | | |
|---|---|---|---|---|---|
|  | NIT | anti-PD-1 | Expected Bliss Additive Value | Actual Observed Value | Interaction |
| Tumor Growth Inhibition | 0.31 | 0.8 | 0.86 | 0.9 | Synergy |

Figure 12:
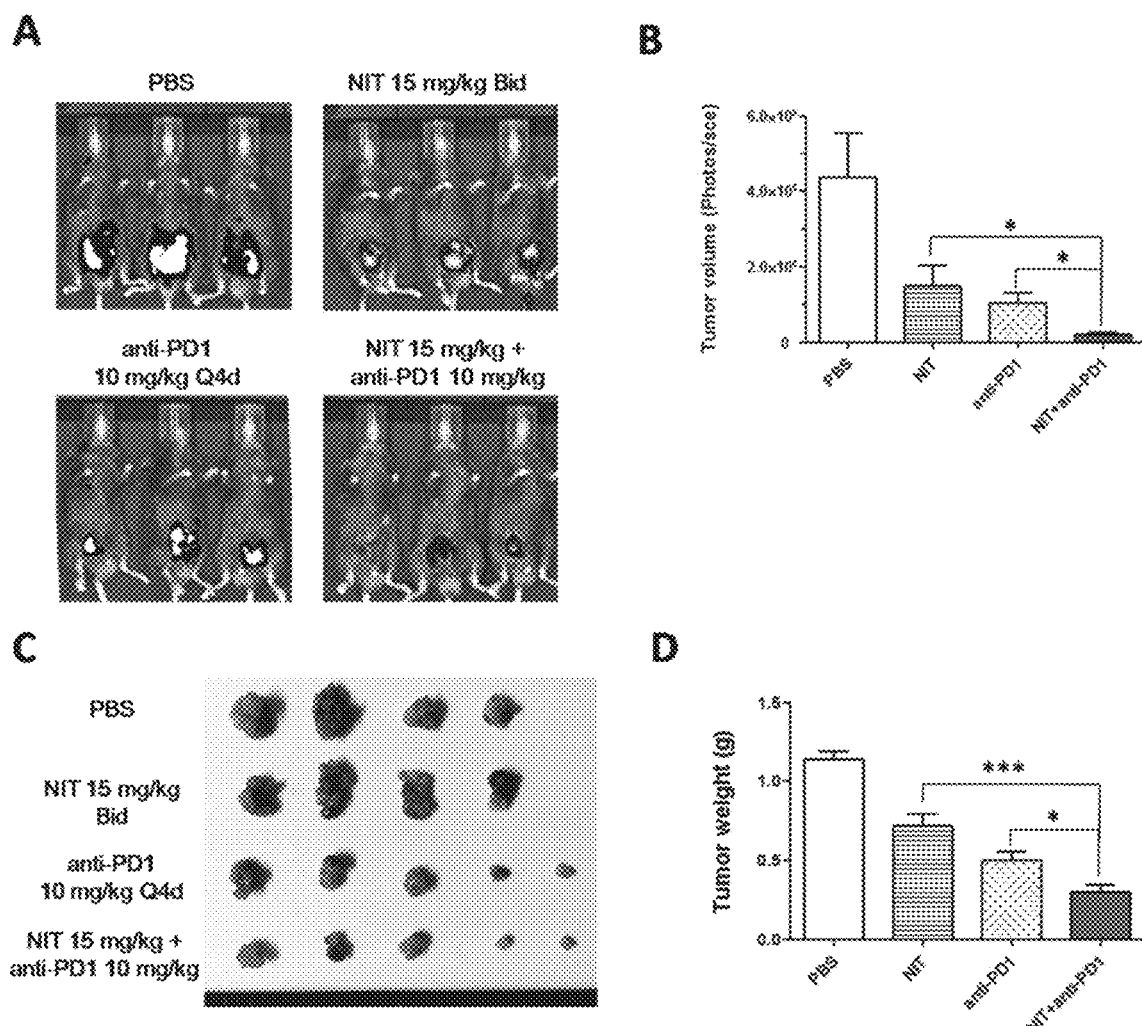
FIG. 12 shows the inhibition of tumor growth by the combination of oral NIT and anti-PD-1 antibody in an orthotopic mouse RM-9-Luc prostate cancer model.

FIG. 12 shows the effect of orally dosed NIT combined with intraperitoneal anti-PD-1 antibody on inhibiting tumor growth in a RM-9-luc orthotopic mouse prostate cancer model. Typical IVIS images for each indicated treatment group are shown in FIG. 12A. The tumor volume of each mouse was determined by region-of-interest analysis of total photons per second. Eight mice were analyzed for each group. As shown in FIG. 12B, 10 mg/kg intraperitoneal anti-PD-1 showed robust tumor growth inhibition (76%), while 15 mg/kg NIT administered orally showed a tumor inhibition rate of 52%. When NIT was combined with anti-PD-1, the tumor inhibition rate was significantly enhanced to 96%, with p values of 0.017 and 0.027 compared to single NIT and anti-PD-1 treatments, respectively. FIG. 12C shows images of tumors collected from each group. The tumor weight of each mouse was determined and is summarized in FIG. 12D. Analysis of tumor weight data revealed that the combination of NIT and anti-PD-1 resulted in significant enhancement of tumor inhibition (74%), compared to single NIT and anti-PD-1 treatments (37% and 56% respectively), with p values of 0.0006 and 0.0111, respectively.

The results of the Bliss independence model calculations of additivity for tumor volume and weight are summarized in Table 22. When NIT was administered in combination with anti-PD-1, its actual observed tumor volume and weight inhibition rate were 0.96 and 0.74, respectively, greater than their Expected Bliss Additive Values (0.89 and 0.72, respectively), suggesting a synergy in tumor inhibition.

TABLE 22

Bliss independence model calculations of additivity for oral
NIT in combination with anti-PD-1 antibody in an orthotopic
mouse RM-9-Luc prostate cancer model.

|  | Single drug | | NIT + anti-PD-1 | | |
| --- | --- | --- | --- | --- | --- |
|  | NIT | anti-PD-1 | Expected Bliss Additive Value | Actual Observed Value | Interaction |
| Tumor Growth Inhibition | 0.52 | 0.76 | 0.89 | 0.96 | Synergy |
| Tumor Weight Proportion | 0.37 | 0.56 | 0.72 | 0.74 | Synergy |

The discovery that NIT has different degrees of synergism with different immunotherapies can be used for the combinational treatment of a variety of solid and blood tumors.

Example 3: Experimental Procedures 3.1 Study Materials

Compounds: NIT, carboplatin, paclitaxel, epirubicin and pirarubicin were purchased from suppliers, and were dissolved in the DMSO to stock solution and store in −20° C. Before use, the stock solutions were diluted to different concentrations of working solutions. The DMSO concentration in working solutions was less than 1%. All cancer cell lines were purchased from vendors.

Cell lines and reagents: The murine bladder cancer cell lines MBT-2 and RM-9 were provided by the American Type Culture Collection (Rockville, MD, USA). All cells were maintained in RPMI-1640 medium supplemented with 10% fetal bovine serum. The cells were cultured at 37° C. in a 5% $CO_2$ atmosphere and routinely passaged by trypsin-EDTA treatment in 100-cm2 flasks containing BCG (81 mg; Connaught substrain, ImmuCyst, Nihou Kayaku, Inc., Tokyo, Japan), and phosphate-buffered saline (PBS) for in vivo studies.

MBT-2 and RM-9 cells stably expressing luciferase (MBT-2-Luc and RM-9-Luc; luciferase L4899 obtained from Sigma-Aldrich Japan G.K.) were generated by transfecting MBT-2 and RM-9 cells with the pGL3-Luc plasmid using a TransIT®-3T3 transfection kit (Mirus Bio LLC, Madison, WI, USA). Cells that stably expressed luciferase were obtained by selection with 500 µg/mL of G418 for two weeks. Following G418 selection, growth medium from MBT-2-Luc and RM-9-Luc was tested for luciferase activity to confirm the expression and secretion of luciferase into the cell medium.

Rat anti-mouse PD-1 mAb (RMP1-14; IgG2a) was purchased from BioXCell (West Lebanon, NH, USA).

Animals: Eight-week-old female C3H/HeN and C57/BL6 mice were obtained from vendors. The mice were maintained at the animal facility in a specific pathogen-free environment with food and water provided ad libitum.

3.2 In Vitro Assays

An MTT assay was used as the test method. An appropriate amount of cells ($2 \times 10^3$/100 µL) was seeded into 96-well plate and incubated at 37° C. in a $CO_2$ incubator overnight for cell adhesion and adaptation. Cancer cells were also seeded in a separate 96-well plate (plate TO), 12 wells/cell line, to measure the OD value at time zero (T0). After overnight adaptation, 20 µL MTT reagent were added per well (final concentration 0.5 mg/mL) to plate TO and incubated at 37° C. for 4 hours. The supernatant medium was pipetted out, and about 150 µL DMSO were added per well. The plate was read on a plate reader using 550 nm as the test wavelength and 630 nm as the reference wavelength to obtain the OD value at time zero (T0). After overnight adaptation, the test compounds and vehicle were added into the plate to treat the cells. The test compounds were tested at 6 concentrations in triplicate wells. The plate was incubated at 37° C. in a $CO_2$ incubator for 48 h. A longer incubation time can be used. 20 µL MTT reagent were added per well and incubated at 37° C. for 4 h. The supernatant medium was pipetted out, and about 150 µL DMSO were added per well. The plate was read on a plate reader (TECAN, Infinite M200) using about 550 nM as the test wavelength and about 630 nM as the reference wavelength. Cell viability (%) was calculated in two ways:

% Viability=$[(T-B)/(C-B)] \times 100\%$

% Viability=$[(T-C_0)/(C-C_0)] \times 100\%$

T: Mean Absorbance of Treatment at various hours;
C: Mean Absorbance of negative Control at various hours;
B: Mean Absorbance of blank well (only culture medium) at various hours;
$C_0$: Mean Absorbance of negative Control at 0 h.

The results are expressed as mean±SD. The $IC_{50}$ was calculated by XLfit software. The test for each compound was independently repeated once.

3.3 In Vivo Effects on the Murine Bladder and Prostate Cancer Models.

To establish the orthotopic bladder cancer tumors, the mice were anesthetized by the intraperitoneal (i.p.) administration of ketamine/xylazine solution at a dose of 0.1 ml/10 g body weight (K113; Sigma-Aldrich Japan G.K., Tokyo, Japan). A 24-gauge Teflon intravenous catheter was subsequently inserted through the urethra into the bladder or prostate using an inert lubricant. In order to prepare the bladder for tumor implantation, a brief acid exposure, followed by alkaline neutralization, promoted a chemical lesion on the bladder wall, performed by the intravesical instillation of 8 µl 1 MOI silver nitrate. This led to the formation of an adequate and controlled diffuse bladder wall lesion. After 15 sec, the content was washed out by transurethral infusion of PBS. The first catheter was removed and a new 24-gauge catheter was inserted in the urethra for intravesical instillation of MBT-2-Luc cells ($5 \times 10^4$ cells mixed with 0.1 ml PBS) and retained for 1.5 h by stitches. Every 10 days, tumor imaging was performed following i.p. administration of luciferin using bioluminescence technology (Xenogen IVIS200 system; Xenogen Corporation, Hopkinton, MA, USA).

For the NIT and BCG combination, the mice carrying orthotopic bladder cancer tumors were randomly divided into six groups: control (PBS), BCG, NIT with consecutive dosing, NIT with consecutive dosing except for a 24-hour break before and after the weekly BCG instillation (48-hour break group), the combination of NIT (consecutive dosing) and BCG, and the combination of NIT (48-hour break) and BCG. Detailed descriptions of the drug dosing are shown in Table 23. According to the tumor imaging results, as determined by the luciferase expression, BCG ($1 \times 10^5$ CFU/100 µL) was administered intravesically once weekly for three weeks. NIT was administrated continuously or with a 48-hour break.

TABLE 23

Drug dosing schematic.

| Groups | Day 1, 8 | Day 2, 9 | Day 3, 10 | Day 4, 11 | Day 5, 12 | Day 6, 13 | Day 7, 14 |
|---|---|---|---|---|---|---|---|
| Group1: vehicle | ΔΔ | ΔΔ ○ | ΔΔ | ΔΔ | ΔΔ | ΔΔ | ΔΔ |
| Group 2: NIT, Consecutive dosing (bid, p.o 30 mg/kg) | ▲▲ | ▲▲ ○ | ▲▲ | ▲▲ | ▲▲ | ▲▲ | ▲▲ |
| Group 3: NIT, 48-h Break/week | ▲ * | * ○ | * ▲ | ▲▲ | ▲▲ | ▲▲ | ▲▲ |
| Group 4: BCG (1 × 10⁵ CFU/100) intravesical administration | ΔΔ | ΔΔ ● | ΔΔ | ΔΔ | ΔΔ | ΔΔ | ΔΔ |
| Group 5: BCG + NIT continuous dosing | ▲▲ | ▲▲ ● | ▲▲ | ▲▲ | ▲▲ | ▲▲ | ▲▲ |
| Group 6: BCG + NIT with 48-h break/week | ▲ * | * ● | * ▲ | ▲▲ | ▲▲ | ▲▲ | ▲▲ |

○: PBS intravesical administration, ●: BCG intravesical administration, Δ: CMC p.o, ▲: NIT p.o, * NIT dosing break for 48 h For the NIT and MMC combination, the mice carrying orthotopic bladder cancer tumors were randomly divided into four groups: control (PBS), NIT, MMC, and the combination of NIT and MMC. Detailed descriptions of the drug dosing are shown in Table

TABLE 24

Drug dosing schematic.

| Groups | Day 1, 8 | Day 2, 9 | Day 3, 10 | Day 4, 11 | Day 5, 12 | Day 6, 13 | Day 7, 14 |
|---|---|---|---|---|---|---|---|
| Group1: vehicle | ΔΔ ○ | ΔΔ | ΔΔ | ΔΔ | ΔΔ | ΔΔ | ΔΔ |
| Group 2: NIT (bid,p.o 15 mg/kg) | ▲▲ ○ | ▲▲ | ▲▲ | ▲▲ | ▲▲ | ▲▲ | ▲▲ |
| Group 3: MMC (q7d, intravesical administration, 1 mg/ml) | ΔΔ ● | ΔΔ | ΔΔ | ΔΔ | ΔΔ | ΔΔ | ΔΔ |
| Group 4: NIT + MMC | ▲▲ ● | ▲▲ | ▲▲ | ▲▲ | ▲▲ | ▲▲ | ▲▲ |

○: PBS intravesical administration, ●: MMC intravesical administration, Δ: CMC p.o, ▲: NIT p.o For the NIT and anti-PD-i combination, the mice carrying orthotopic bladder cancer tumors were randomly divided into four groups: control (PBS), NIT, anti-PD-1, and the combination of NIT and anti-PD-i. Detailed descriptions of the drug dosing are shown in Table 25.

TABLE 25

Drug dosing schematic.

| Groups | Day 1, 6, 11 | Day 2, 7, 12 | Day 3, 8, 13 | Day 4, 9, 14 | Day 5, 10, 15 |
|---|---|---|---|---|---|
| Group 1: vehicle | ΔΔ ○ | ΔΔ | ΔΔ | ΔΔ | ΔΔ |
| Group 2: NIT (bid, p.o 15 mg/kg) | ▲▲ ○ | ▲▲ | ▲▲ | ▲▲ | ▲▲ |
| Group 3: anti-PD-1 (q5d, intraperitoneal-administration, 10 mg/kg) | ΔΔ ● | ΔΔ | ΔΔ | ΔΔ | ΔΔ |
| Group 4: NIT + anti-PD-1 | ▲▲ ● | ▲▲ | ▲▲ | ▲▲ | ▲▲ |

○: PBS intraperitoneal administration, ●: anti-PD-1 intraperitoneal administration, Δ: CMC p.o, ▲: NIT p.o To establish the orthotopic prostate cancer tumors, C57/BL6 mice were intraperitoneally anesthetized with a ketamine/xylazine solution at a dose of 0.1 ml/10 g body weight (K113; Sigma-Aldrich Japan G.K., Tokyo, Japan). A low abdominal transverse incision was made, and the bilateral dorsal lobes of prostate were exposed. Following the trypsinization of RM-9-Luc cells, 5.0×10³ cells in 10 μl of Hanks' balanced salt solution were injected using a new 24-gauge catheter directly into the right dorsal lobe of the prostate. A clearly recognizable bleb within the injected prostatic lobe was considered as a sign of a technically satisfactory injection. The abdominal wound was closed with stainless steel clips (Autoclip; Becton Dickinson Co., Sparks, MD). One week after the RM-9-Luc cell injection, when the tumor diameter reached 5 mm, the mice carrying orthotopic prostate cancer tumors were randomly divided into four groups: control (PBS), NIT, anti-PD-1, and the combination of NIT and anti-PD-1. Detailed descriptions of the drug dosing are shown in Table 26.

TABLE 26

Drug dosing schematic.

| Groups | Day 1, 5, 9, 13 | Day 2, 6, 10, 14 | Day 3, 7, 11, 15 | Day 4, 8, 12, 16 |
|---|---|---|---|---|
| Group 1: vehicle | ΔΔ ○ | ΔΔ | ΔΔ | ΔΔ |
| Group 2: NIT (bid, p.o 15 mg/kg) | ▲▲ ○ | ▲▲ | ▲▲ | ▲▲ |
| Group 3: anti-PD-1 (q4d, intraperitoneal-administration, 10 mg/kg) | ΔΔ ● | ΔΔ | ΔΔ | ΔΔ |
| SGroup 4: NIT + anti-PD-1 | ▲▲ ● | ▲▲ | ▲▲ | ▲▲ |

○: PBS intraperitoneal administration, ●: anti-PD-1 intraperitoneal administration, Δ: CMC p.o, ▲: NIT p.o The mice received i.p. injections of luciferin, and the luciferase expression in the tumors was measured by the Xenogen IVIS200 System. The mice were killed using $CO_2$ for euthanasia and according to the guidelines for the euthanasia of animals (Edition, 2013).

3.4 Statistical Analysis.

Data from all quantitative assays are expressed as the mean±standard deviation and were analyzed statistically using a one-way analysis of variance (ANOVA) and the independent-samples t test. Statistical calculations were performed using GraphPad Prism 5. P values of less than 0.05 were considered statistically significant.

Additivity was determined using the fractional product concept or Bliss Independence model: $E_{xy}=E_x+E_y-(E_xE_y)$, where $E_{XY}$ is the additive effect of the 2 compounds x and y as calculated by the product of the individual effect of the 2 compounds, $E_x$ and $E_y$. Synergy was established when the actual observed tumor inhibition value was greater than the expected tumor inhibition value determined by the Bliss Independence model (20).

REFERENCES

1. Pelletier C, Prognon P, Bourlioux P Roles of divalent cations and pH in mechanism of action of nitroxoline against *Escherichia coli* strains. *Antimicrob Agents Chemother.* 1995; 39(3):707-13.
2. Fraser R S, Creanor J. The mechanism of inhibition of ribonucleic acid synthesis by 8-hydroxyquinoline and the antibiotic lomofungin *Biochem J.* 1975; 147(3):401-10.

3. Adlard P A at al. Rapid restoration of cognition in Alzheimer's transgenic mice with 8-hydroxy quinoline analogs is associated with decreased interstitial A-beta. *Neuron.* 2008; 59(1):43-55.
4. Shim J S, et al. Effect of nitroxoline on angiogenesis and growth of human bladder cancer. *J Natl Cancer Inst.* 2010; 102(24):1855-73.
5. Chang W L et al. Repurposing of nitroxoline as a potential anticancer agent against human prostate cancer: a crucial role on AMPK/mTOR signaling pathway and the interplay with Chk2 activation. *Oncotarget.* 2015; 6(37): 39806-20.
6. Jiang H. et al. Nitroxoline (8-hydroxy-5-nitroquinoline) is more a potent anti-cancer agent than clioquinol (5-chloro-7-iodo-8-quinoline) *Cancer Letters* 2011; 312:11-17.
7. Ding W Q, Liu B, Vaught J L, Yamauchi H, and Lind S E. Anticancer activity of the antibiotic clioquinol. *Cancer Res* 2005; 65:3389-95.
8. Whiteside T L, Inhibiting the Inhibitors: Evaluating Agents Targeting Cancer Immunosuppression. *Expert OpinBiolTher.* 2010; 10(7): 1019-1035.
9. Fuge O, Vasdev N, Allchorne P, Green J S, Immunotherapy for bladder cancer. *Res Rep Urol.* 2015; 7:65-79.
10. Huang P, Ma C, Xu P, Guo K, Xu A, Liu C, Efficacy of intravesical *Bacillus* Calmette-Guerin therapy against tumor immune escape in an orthotopic model of bladder cancer. *ExpTher Med.* 2015; 9(1):162-166.
11. Pardoll D M. The blockade of immune checkpoints in cancer immunotherapy. *Nat Rev Cancer.* 2012; 12(4): 252-64.
12. Krummel M F, Allison J P. CD28 and CTLA-4 have opposing effects on the response of T cells to stimulation. *J Exp Med.* 1995; 182(2):459-65.
13. Hamid O, Robert C, Daud A, Hodi F S, Hwu W J, Kefford R. et al. Safety and tumor responses with lambrolizumab (anti-PD-1) in melanoma. *N Engl J Med.* 2013; 369(2):134-44.
14. Freeman G J, Long A J, Iwai Y et al. Engagement of the PD-1 immunoinhibitory receptor by a novel B7 family member leads to negative regulation of lymphocyte activation. *J Exp Med.* 2000; 192:1027-1034.
15. Hawkes E A, Grigg A, Chong G. Programmed cell death-1 inhibition in lymphoma. *Lancet Oncol.* 2015; 16(5):e234-45.
16. Liu X, Shin N, Koblish H K, et al. Selective inhibition of IDO1 effectively regulates mediators of antitumor immunity. *Blood.* 2010; 115:3520-3530.
17. Opitz C A, Litzenburger U M, Opitz U, et al. The indoleamine-2,3-dioxygenase (IDO) inhibitor 1-methyl-D-tryptophan upregulates IDO1 in human cancer cells. *PloS One.* 2011; 6:e19823.
18. Muller A J, Prendergast G C. Marrying immunotherapy with chemotherapy: why say IDO?*Cancer Res.* 2005; 65:8065-8068.
19. Ting-Chao Chou, Theoretical Basis, Experimental Design, and Computerized Simulation of Synergism and Antagonism in Drug Combination Studies. *Pharmacol Rev* 2006; 58:621-681.
20. Yan H, Zhang B, Li S, Zhao Q. A formal model for analyzing drug combination effects and its application in TNF-alpha-induced NFkappaB pathway. *BMC Syst Biol.* 2010; 4:50.

The invention claimed is:

1. A method of treating bladder cancer comprising administering to a subject in need thereof an effective amount of nitroxoline, an analogue or pharmaceutically acceptable salt thereof, and an effective amount of a chemotherapeutic agent, wherein the combination of nitroxoline, the analogue or pharmaceutically acceptable salt thereof and the chemotherapeutic agent results in a synergistic effect, wherein the analogue is selected from the group consisting of oxyquinoline, clioquinol, and iodoquinol, and wherein the chemotherapeutic agent is selected from the group consisting of carboplatin, paclitaxel, mitomycin C, epirubicin, and pirarubicin.

2. The method of claim 1, wherein the chemotherapeutic agent is administered intravesically.

3. The method of claim 1, wherein the nitroxoline, analogue, or pharmaceutically acceptable salt thereof and the chemotherapeutic agent are administered by way of the simultaneous, sequential or separate administration.

4. The method of claim 1, wherein the effective amount of nitroxoline, the analogue or pharmaceutically acceptable salt thereof is 100 mg to 1600 mg administered orally per day, and carboplatin, mitomycin C, epirubicin, or pirarubicin is administered intravesically in a bladder instillation fluid at a concentration of 0.1 mg/mL to 5 mg/mL.

5. The method of claim 1, wherein the effective amount of nitroxoline, the analogue or pharmaceutically acceptable salt thereof is 100 mg to 1600 mg administered orally per day, and, paclitaxel is administered intravesically in a bladder instillation fluid at a concentration of 0.5 mg/mL to 10 mg/mL.

6. A kit comprising an effective amount of nitroxoline, an analogue, or a pharmaceutically acceptable salt thereof, an effective amount of a chemotherapeutic agent, and one or more pharmaceutically acceptable carriers for treating bladder cancer in a subject in need thereof, wherein the analogue is selected from the group consisting of oxyquinoline, clioquinol, and iodoquinol, and wherein the chemotherapeutic agent is selected from the group consisting of carboplatin, paclitaxel, mitomycin C, epirubicin, and pirarubicin.

7. The kit of claim 6, wherein the kit further contains instructions on using a combination of the effective amount of nitroxoline, the analogue or pharmaceutically acceptable salt thereof and the effective amount of the chemotherapeutic agent.

8. The kit of claim 6, wherein the effective amount of nitroxoline,
the analogue or pharmaceutically acceptable salt thereof and the effective amount of the chemotherapeutic agent are present in one composition, or present in separate compositions.

9. A composition comprising an effective amount of nitroxoline, an analogue, or a pharmaceutically acceptable salt thereof, an effective amount of a chemotherapeutic agent, and one or more pharmaceutically acceptable carriers for treating bladder cancer in a subject in need thereof, wherein the analogue is selected from the group consisting of oxyquinoline, clioquinol, and iodoquinol, and wherein the chemotherapeutic agent is selected from the group consisting of carboplatin, paclitaxel, mitomycin C, epirubicin, and pirarubicin.

* * * * *